US012343127B2

(12) United States Patent
Andiappan et al.

(10) Patent No.: US 12,343,127 B2
(45) Date of Patent: Jul. 1, 2025

(54) NON-CONTACT SENSING OF VITAL SIGNS

(71) Applicant: Intel Corporation, Santa Clara, CA (US)

(72) Inventors: Rajasekaran Andiappan, Raseborg (FI); Guoqing Zhang, Tampere (FI); Ofir Mulla, Petach Tikva (IL); Lakshman Krishnamurthy, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 181 days.

(21) Appl. No.: 17/724,195

(22) Filed: Apr. 19, 2022

(65) Prior Publication Data

US 2023/0092182 A1  Mar. 23, 2023

(51) Int. Cl.
| | |
|---|---|
| *A61B 5/05* | (2021.01) |
| *A61B 5/00* | (2006.01) |
| *A61B 5/0205* | (2006.01) |
| *A61B 5/024* | (2006.01) |
| *A61B 5/08* | (2006.01) |
| *A61B 5/11* | (2006.01) |
| *G06V 20/20* | (2022.01) |
| *G06V 40/20* | (2022.01) |

(52) U.S. Cl.
CPC .............. *A61B 5/05* (2013.01); *A61B 5/0205* (2013.01); *A61B 5/02444* (2013.01); *A61B 5/0816* (2013.01); *A61B 5/1126* (2013.01); *A61B 5/1128* (2013.01); *A61B 5/7221* (2013.01); *G06V 20/20* (2022.01); *G06V 40/20* (2022.01)

(58) Field of Classification Search
USPC .......................................................... 600/301
See application file for complete search history.

(56) References Cited

U.S. PATENT DOCUMENTS

| | | | |
|---|---|---|---|
| 2013/0030257 A1* | 1/2013 | Nakata | G01S 13/87 600/407 |
| 2020/0121215 A1 | 4/2020 | Hyde et al. | |

OTHER PUBLICATIONS

Chian et al., "Vital Signs Identification System with Doppler Radars and Thermal Camera", IEEE Transactions on Biomedical Circuits and Systems, US, vol. 16, No. 1, pp. 153-167, DOI: 10.1109/TBCAS.2022.3147827, published Feb. 1, 2022, 15 pages.

European Patent Office, "Extended European Search Report," issued in connection with European Patent Application No. 23157864.2-1113, dated Sep. 18, 2023, 10 pages.

Shafiq et al., "Surface Chest Motion Decomposition for Cardiovascular Monitoring," School of Electronics Engineering, College of IT Engineering, Kyungpook National University, Daegu, South Korea, May 28, 2014 9 Pages.

* cited by examiner

*Primary Examiner* — Nadia A Mahmood
(74) *Attorney, Agent, or Firm* — HANLEY, FLIGHT & ZIMMERMAN, LLC

(57) ABSTRACT

Methods, apparatus, systems, and articles of manufacture are disclosed for non-contact sensing of vital signs. An example electronic device to measure vital signs includes a camera to capture an image; a radar antenna to transmit and receive radar signals; and processing circuitry to: identify a subject in the image; identify a location of the subject in an environment; control the radar antenna to steer the radar signals toward the location; and determine a vital sign of the subject based on a reflected radar signal.

21 Claims, 11 Drawing Sheets

NON-CONTACT SENSING OF VITAL SIGNS

FIELD OF THE DISCLOSURE

This disclosure relates generally to measuring vital signs of a patient and, more particularly, to non-contact sensing of vital signs.

BACKGROUND

Conventional clinical methods use contact sensors to measure vital signs of a patient. Wearable devices such as activity trackers and smart watches include contact sensors to measure vital signs.

BRIEF DESCRIPTION OF THE DRAWINGS

In general, the same reference numbers will be used throughout the drawing(s) and accompanying written description to refer to the same or like parts. The figures are not to scale.

DETAILED DESCRIPTION

Figure 1:
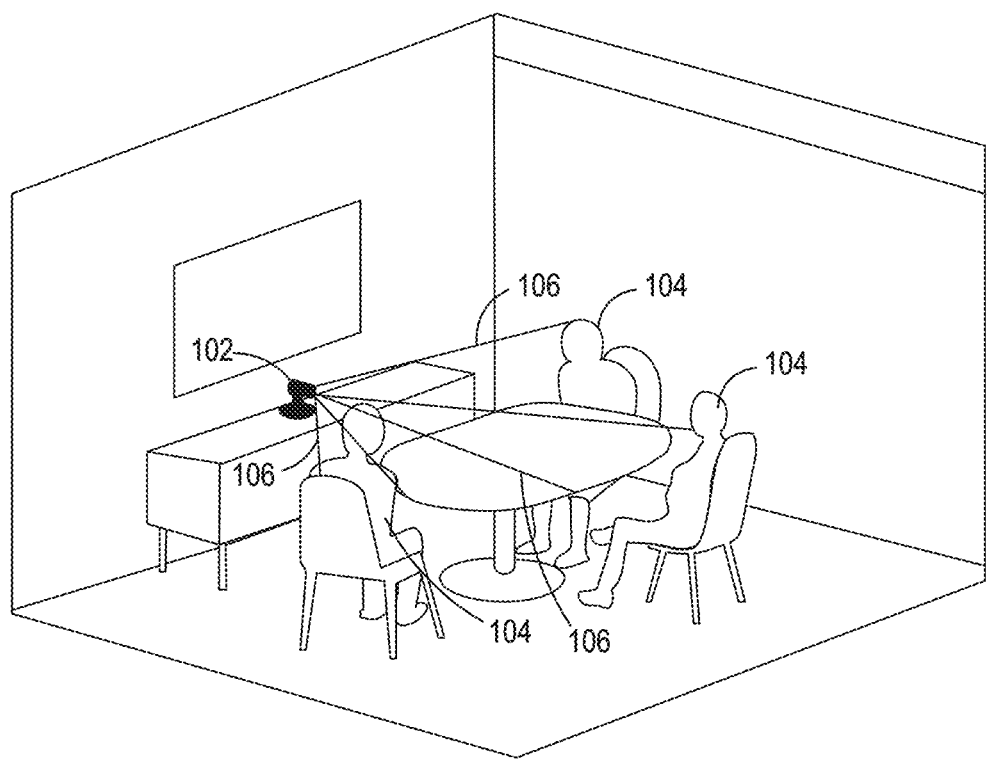
FIG. 1 is a schematic illustration of an example environment including an example electronic device to measure vital signs of patients.

Vital signs are important measurements that provide critical information about human bodies. Vital signs measure a body's basic, life sustaining functions. Monitoring of vital signs provides important information about a person's well-being, presence of a disease or other underlying health problems, detection of symptomless medical problems, and/or recovery progression. Four primary vital signs include body temperature, heart rate or pulse, respiratory rate, and blood pressure. Vital signs also may include pain, pupillary dilation, menstrual cycle, blood oxygenation percentage, blood glucose level, end-tidal carbon dioxide, shortness of breath, gait speed, and delirium. The ranges for a person's vital signs depend on age, weight, gender, and overall health. Examples disclosed herein may be used to measure vital signs and/or other activity including other types of motor behavior, joint positioning, atrial fibrillation, sleep, stress, pulmonary congestion, etc.

Detecting, sensing, measuring, or monitoring of vital signs typically includes equipment such as, for example, a thermometer, a sphygmomanometer, a stethoscope, and/or other types of contact sensors. The use of contact sensors is not practical for long term monitoring nor for continuous monitoring in which the method of measurement does not affect a person's mobility. Wearables such as activity trackers and smart watches have contact sensors for vital signs measurement. Wearables are not suited for clinical patients or elderly people who may not be able to operate smart handhelds and/or whose ability, durability, limitations, and/or conditions keep them under continuous monitoring.

Wireless vital signs monitoring does not suffer from the constraints of wearables and other contact sensors such as, for example, power source limitations and/or a need for a companion smart device to manage the wearables and/or other contact sensors. Radar is an example technology that can be used to wirelessly detect vital signs. Wireless vital sign detection using radar do not require the attachment of sensors to the subject's body. However, some products that are radar based are limited with the amount of information that they can supply and limited in reliability when the subject moves around the living space or other environment. In such situations, reliability of the non-contact vital signs measurement is enhanced by placing the subject in front of a narrow band radar for a specified duration and distance until the vital signs are computed. However, the radar beams are fixed and the field of view of narrow band of radar limits the coverage of the environment being monitored. Also, subjects typically must remain still during the measurement process. Continuous non-contact measurements of one or more persons moving around the same environment are not feasible with a single measurement setup. Contact measurement methods and fixed beam measurement methods are not ambient because such measurement methods do not gather data without interfering with the subject's movement, comfort, and/or other activity in the environment.

Example apparatus, systems, methods, and articles of manufacture disclosed herein use inferences from an example vision subsystem for detecting and tracking subjects in an environment to perform adaptive beamforming of an example radar subsystem. In examples disclosed herein, a vision subsystem that includes, for example, a camera gathers data about a subject, which is then used by the radar subsystem to focus or steer its array of antennas toward the subject for vital signs measuring. In some examples, the vision subsystem is primarily used to detect a human, a pose of the human, a location in space of the human, and/or an activity of the human. The radar subsystem performs radar beamforming to focus a maximum radio frequency wave on the subject's chest area to perform measurement with increased signal-to-noise ratio than could be achieved without such beamforming.

In some examples disclosed herein, logic circuitry to adjust radar antenna gains to focus energy (e.g., maximum energy) on a subject to enable non-contact vitals measurement despite movement of the subject across a larger area of the environment. This advancement provides an ambient monitoring system that can be integrated to client devices such as, for example, a laptop or other computing devices. Some examples disclosed herein can be incorporated into a standalone monitoring device and/or application.

Examples disclosed herein enable continuous and reliable contactless vital signs sensing. Examples disclosed herein enable non-contact vital signs sensing for multiple people. In addition, examples disclosed herein enable non-contact vital signs sensing for one or more people moving around in the environment. Thus, examples disclosed herein are ambient and are human movement agnostic because vital signs data is gathered without interfering with the subject's movement, comfort, and/or other activity in the environment.

In some examples, identification and tracking of one subject or multiple subjects over time occurs, and a display may present images of the subject in the environment that are augmented with vital sign data overlaying or embedded in the image over or near the subject. This presentation makes vital sign information related to a subject readily observable by a health care professional, caretaker, or other interested party. In some examples, human activity, mobility, and/or vital signs information may be monitored without storing and/or transmitting images, which may preserve privacy.

In some examples, the fusion of vison and radar helps filter out non-reliable radar data and may remove ghost effect caused by radar reflections.

Throughout this patent, a "subject" whose vital signs are measured or to be measured may be referred to interchangeably as a subject, a person, people, a human, a patient, or a body. Examples disclosed here may also be implemented with non-human animals.

Throughout this patent, an "environment" in which the subject who is monitored is located may be referred to interchangeably as an environment, a space, an area, a living space, a home, a building (of any type), a room (of any type), a hospital, a doctor's office, or a clinic. A "location" or a "position" refers to a placement of the subject within the environment. Thus, an environment includes many locations or positions.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name.

As used herein, "approximately" and "about" refer to dimensions that may not be exact due to manufacturing tolerances and/or other real world imperfections. For example, the dimensions may be within a tolerance range of +/−10%. As used herein "substantially real time" refers to occurrence in a near instantaneous manner recognizing there may be real world delays for computing time, transmission, etc. Thus, unless otherwise specified, "substantially real time" refers to real time+/−1 second.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, "processor circuitry" is defined to include (i) one or more special purpose electrical circuits structured to perform specific operation(s) and including one or more semiconductor-based logic devices (e.g., electrical hardware implemented by one or more transistors), and/or (ii) one or more general purpose semiconductor-based electrical circuits programmed with instructions to perform specific operations and including one or more semiconductor-based logic devices (e.g., electrical hardware implemented by one or more transistors). Examples of processor circuitry include programmed microprocessors, Field Programmable Gate Arrays (FPGAs) that may instantiate instructions, Central Processor Units (CPUs), Graphics Processor Units (GPUs), Digital Signal Processors (DSPs), XPUs, or microcontrollers and integrated circuits such as Application Specific Integrated Circuits (ASICs). For example, an XPU may be implemented by a heterogeneous computing system including multiple types of processor circuitry (e.g., one or more FPGAs, one or more CPUs, one or more GPUs, one or more DSPs, etc., and/or a combination thereof) and application programming interface(s) (API(s)) that may assign computing task(s) to whichever one(s) of the multiple types of the processing circuitry is/are best suited to execute the computing task(s).

FIG. 1 is a schematic illustration of an example environment 100 including an example electronic device 102 used to measure vital signs of people. In the example of FIG. 1, there are three subjects 104 being monitored. The electronic device 102 includes a vision subsystem that identifies the respective locations of the subjects 104 in the environment 100. The electronic device 102 also includes a radar subsystem that sequentially or simultaneously focuses respective radar beams 106 toward the respective subjects 104.

The subjects 104 are seated in the environment but the examples disclosed herein may detect vital signs as the subjects 104 move about the environment 100. Thus, the subjects 104 are not required to sit at a specific height, at a specific distance, and/or with a specific pose relative to the field of view of the radar. The subjects 104 are able to move because the field of view of radar and the direction and angle of the transmission beam(s) of the radar is not fixed. The direction and angle of the transmission beam(s) of the radar is (are) adjustable. While the subject 104 is moving or walking, the vision subsystem can track activity and movement, and this information is used to focus the radar beam by steering an antenna of the radar. This focusing may be continuous. Alternatively, refocusing may occur at a desired frequency that is sufficient for measurement and/or emulates continuous refocusing. Moreover, more than one beam may be focused such that different beams are focused on different subjects. Alternatively, the same beam may be moved from subject to subject to sequentially take measurements of different individuals. Thus, examples disclosed herein enable reliable contactless vital signs sensing for several subjects 104 in the same environment 100 and/or when one or more of the subjects 104 are moving around.

Figure 2:
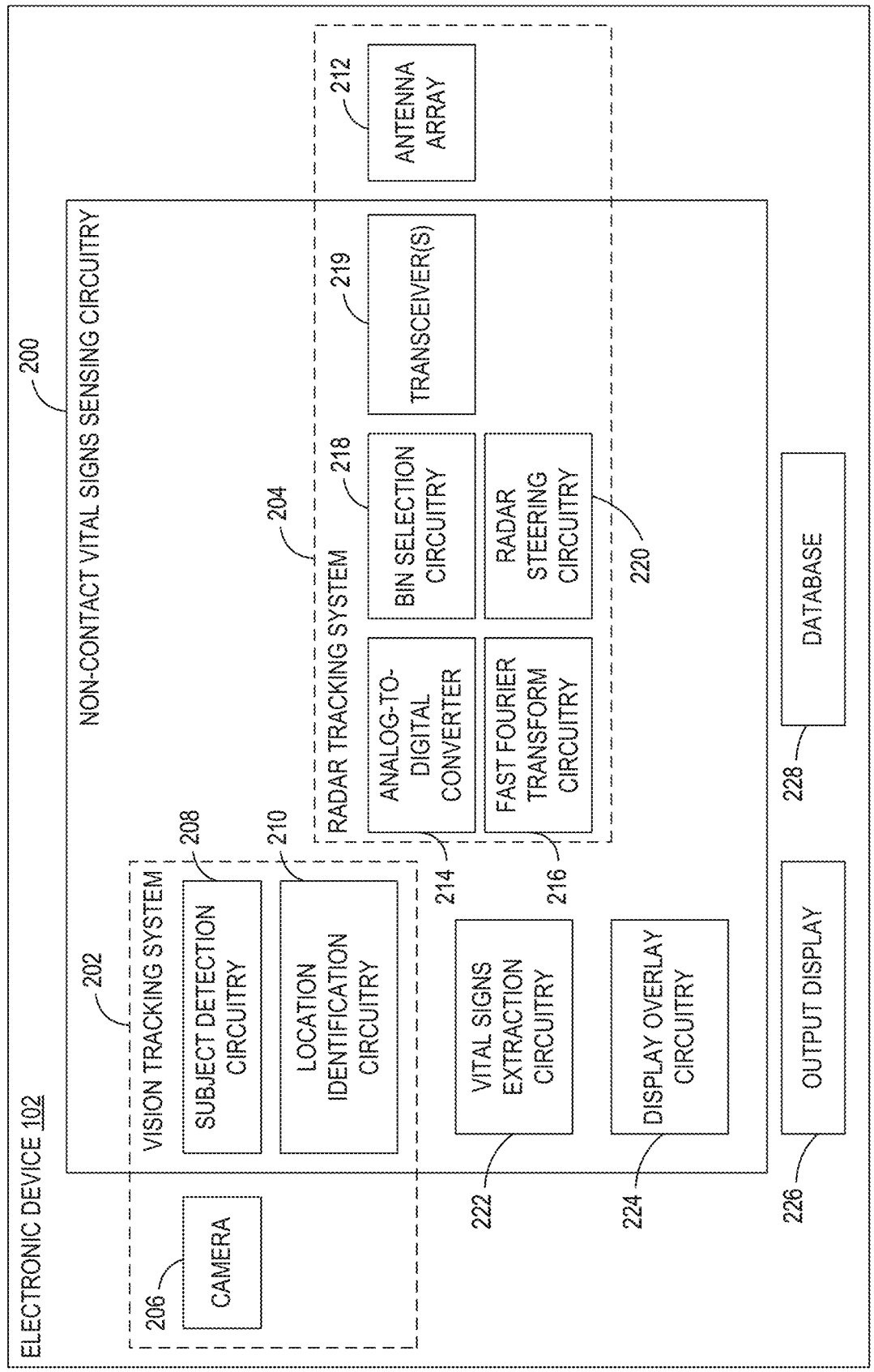
FIG. 2 is a block diagram of an example implementation of the electronic device of FIG. 1 including example non-contact vital sensing circuitry.

FIG. 2 is a block diagram of an example implementation of the example electronic device 102 of FIG. 1 including example non-contact vital signs sensing circuitry 200. The vision subsystem of the electronic device 102 is implemented by the example vision tracking system 202 of FIG. 2, and the radar subsystem of the electronic device 102 is implemented by the example radar tracking system 204 of FIG. 2. The vision tracking system 202 includes an example camera 206, example subject detection circuitry 208, and example location identification circuitry 210. The radar tracking system 204 includes an example antenna array 212, an example analog-to-digital converter 214, example fast Fourier transform (FFT) circuitry 216, example bin selection circuitry 218, an example transceiver 219 (or multiple transceivers), and example radar steering circuitry 220. The non-contact vital signs sensing circuitry 200 also includes example vital signs extraction circuitry 222 and example display overlay circuitry 224. The electronic device 102 includes an example output display 226 and an example database 228. The different circuitry identified in FIG. 2 can individually, collectively, and/or in different subcombinations implemented by processor circuitry programmed with the instructions represented by the flowcharts herein.

To measure one or more vital signs from the subject 104, the electronic device 102 uses the camera 206 to obtain an image of the environment 100 or of a portion of the environment 100. In some examples, the camera 206 obtains multiple images over time (e.g., video), which may be used to track the subject 104 as the subject moves about the environment 100. In some examples, the camera 206 is an RGB color camera. In some examples, the camera 206 may be any type of visible imaging sensor. In some examples, the camera 206 may be an infrared (IR) camera such as a forward-looking infrared (FLIR) thermal camera, an RGB-IR camera, etc. Thus, in some examples, the vision tracking system 202 employs infrared technology. Infrared technology enhances the capabilities of the vision tracking system 202 in dark environments such as at night.

Figure 6:
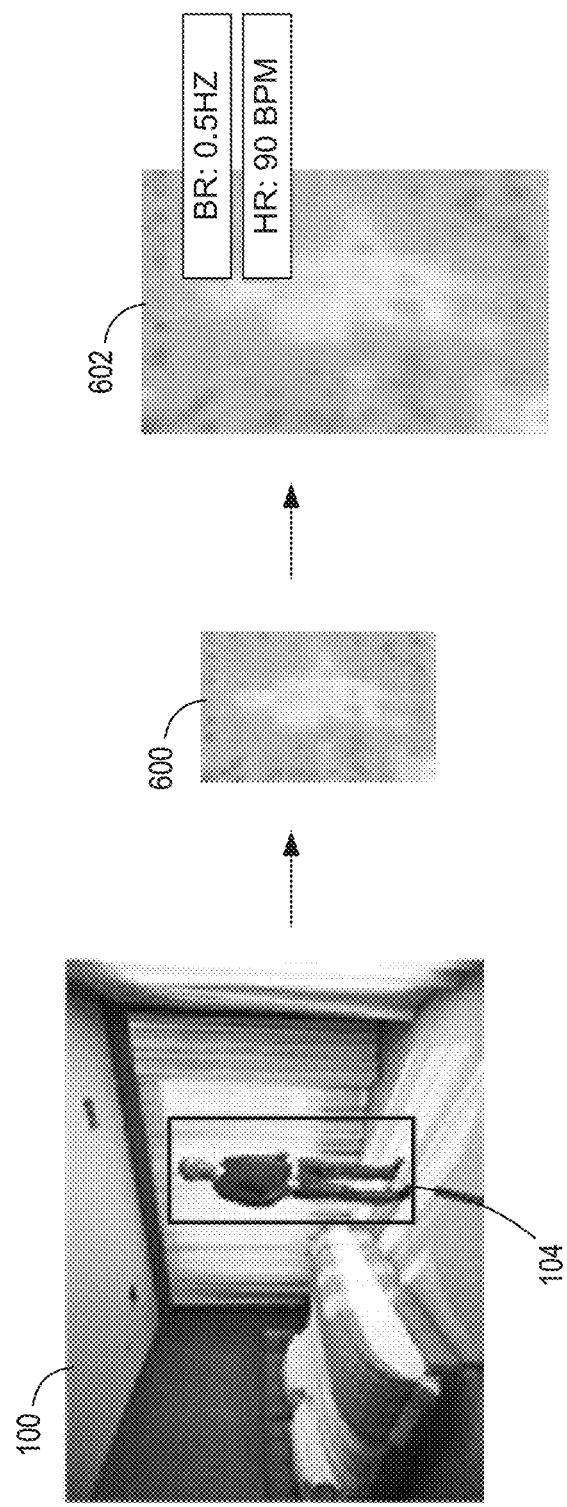
FIG. 6 is an example augmentation of an image.

The subject detection circuitry 208 is communicatively coupled to the camera 206 and accesses, receives, retrieves, or otherwise obtains one or more of the images captured by the camera 206. In some examples, the subject detection circuitry 208 analyzes colors of pixels in the image and/or shapes in the image to identify a subject 104 based on human form of the subject 104. In some examples, an artificial neural network such as, for example, a deep neural network (DNN) may be used for human detection. The DNN may be implemented by processor circuitry to analyze the images to produce a two-dimensional (2D) bounding box of the detected human such as, for example, as shown in FIG. 6. More than one box may be present if more than one subject is detected with one box assigned to each subject. In other examples, other types of artificial intelligence may be used to identify the subjects 104.

Although multiple subjects may be identified and tracked, the following description focuses on one subject 104 for ease of discussion. It is to be understood that the discussion applies equally to instances of tracking more than one subject. The location identification circuitry 210 identifies a location of the subject 104 in the environment. For example, the location identification circuitry 210 may determine x, y, z coordinates of the environment 100 and determine the corresponding coordinates for the pixels representing the subject 104. Additionally or alternatively, the location identification circuitry 210 may identify the location of the subject 104 in the environment 100 based on an angle of the subject 104 in the image relative to the center of a field of view of the camera 206. In some examples, the location identification circuitry 210 uses the 2D bounding box identified by the subject determination circuitry 208, identifies pixel location locations related to the box, and calculates an angle of the subject 104 based on the pixel location. The radar steering circuitry 220 steers the antenna array 212 to measure the range to the subject 104. The location identification circuitry 210 calculates the x, y, z coordinates of the subject 104 with the angle and range information. The vision tracking system 202 saves metadata related to the identification and location of the subject 104 in, for example, the database 228.

Figure 3B:
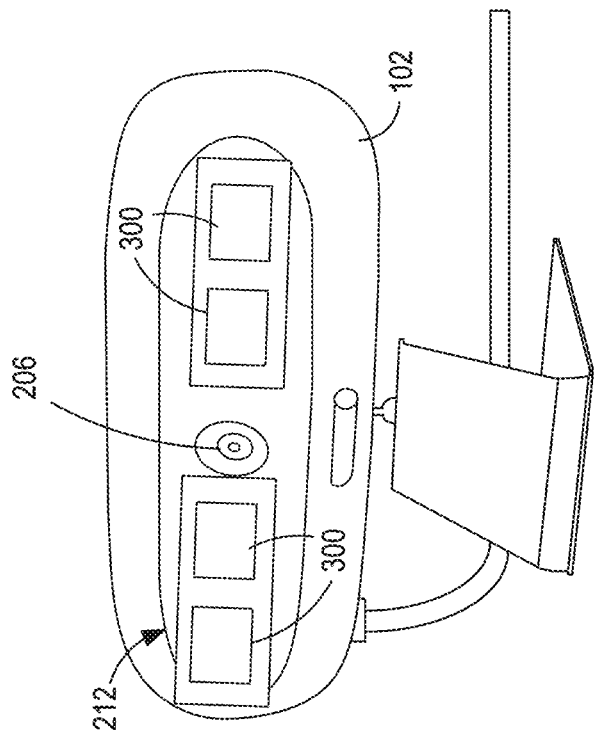
FIGS. 3A and 3B are example implementations of the electronic device of FIG. 1 with the camera and antenna array of FIG. 2
Figure 3A:
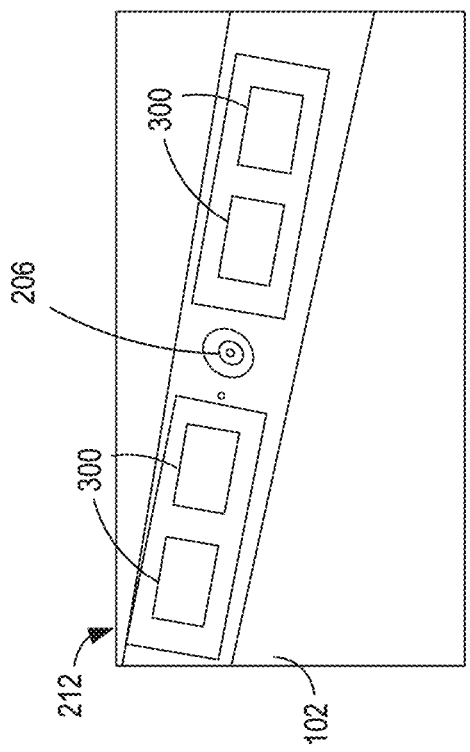

The radar steering circuitry 220 uses the location information from the vision tracking system 202 to steer the antenna array 212 in the direction of the location of the subject 104. The antenna array 212 communicates with the one or a plurality of transceivers 219. FIGS. 3A and 3B shows example implementations of the electronic device 102 including the antenna array 212 that has a plurality of transmitters or antennas 300. The antennas 300 emit or transmit radar signals and receive reflected radar signals or echo signals that are derived from the transmitted radar signals once the transmitted radar signals reflect off an object (e.g., off a person). The antennas 300 are excited by corresponding transceivers 219 and deliver detected reflected signals to the transceivers 219. The transceivers 219 are communication circuitry, modulators, and/or demodulators that drive or excite the antennas 300 to emit energy and/or interpret the signals in or output by the antennas 300.

In FIG. 3A, the electronic device 102 is a laptop. In FIG. 3B, the electronic device 102 is a standalone device. In each example of FIGS. 3A and 3B, the antenna array 212 includes two antennas 300 aligned on each side of the camera 206. However, in other examples, there may be a different number of antennas 300 on one side than on the other side of the camera 206 including, in some examples, no antennas 300 on one side of the camera 206. In some examples, the antenna array 212 is not positioned around the camera 206. In some examples, there are multiple rows of antennas 300. In some examples, the antennas 300 are irregularly placed such that antennas of the antenna array 212 are not strictly aligned in rows and/or columns.

Steering of the antenna array 212 of the radar is to cause a change in the azimuth and elevation of the radar to keep a maximum of transmitted power over the chest area of the subject 104. To steer the antenna array 212 only a subset of the antennas 300 are energized to emit the radar beam. The subset of antennas 300 that are energized to emit the radar beam are selected based on the location of the subject 104. For example, radar beams emanate outward in a cone from the source, i.e., the individual antennas 300. The antennas 300 with beams whose cones cover the location or near the location of a tracked subject are activated to effectively steer the antenna array 212 to the location. Thus, in this example, the steering of the antenna array 212 is not a mechanical movement of the antenna array 212 but, rather, occurs via a change in selection of the set or subset of the antennas 300 to energize.

The selected subset of antennas 300 collectively operate to transmit (e.g., form) the radar beam or radar signals. The radar signals reflect off objects in the environment 100. The selected subset of antennas 300 or all the antennas 300 of the antenna array 212 receive the reflected radar signals. The reflected radar signals are communicated from the antenna array 212 to the transceiver(s) 219.

The reflected radar signals undergo signal processing. For example, the analog-to-digital converter 214 converts the reflected radar signals, which are analog signals, into a digital signal. The FFT circuitry 216 performs a fast Fourier transform on the reflected radar signals and provides a representation of the reflected radar signals across different frequencies. That is, the FFT circuitry 216 transforms the reflected radar signals from the time domain to the frequency domain. The reflected radar signals include different frequencies. Peaks in the frequency domain correlate to objects in the environment. In some examples, a peak represents an object in the environment. In other examples, multiple objects may cause one peak in the FFT if, for example, their respective distances are less than the resolution that the radar can differentiate and/or if the objects are in the same range-bin (as disclosed further herein). Objects that are closer to the antenna array 212 have a relatively lower frequency peak. Objects that are farther from the antenna array 212 have a relatively higher frequency peak.

The bin selection circuitry 218 groups the frequencies into a plurality of bins (also referred to herein as range-bins). The bins correlate to distances from the antenna array 212 and, therefore, locations within the environment 100. Thus, a first bin (or group of bins) represents a first distance from the antenna array 212. A second bin (or group of bins) represents a second distance from the antenna array 212, the second distance different than the first distance. The number of bins correlated with the resolution of the antenna array 212. For example, more bins are associated with more discrete distances and a higher resolution antenna array 212. Fewer bins are associated with less discrete distances and a lower resolution antenna array 212.

Figure 4A:
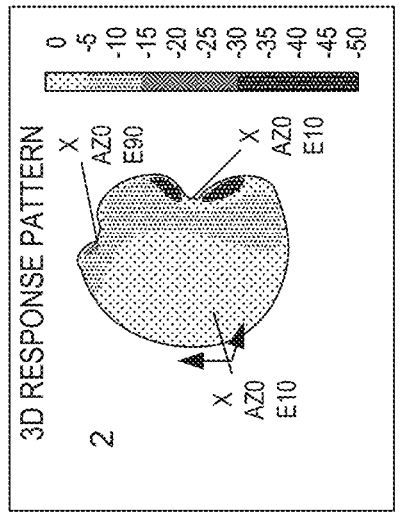
FIGS. 4A-4D are graphic visualizations of radar radiation patterns of radar signals in three-dimensional space.
Figure 4C:
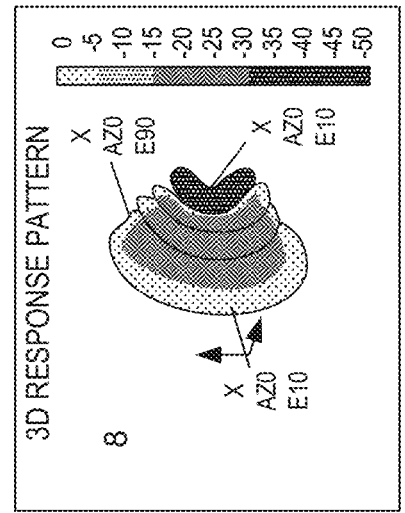
Figure 4B:
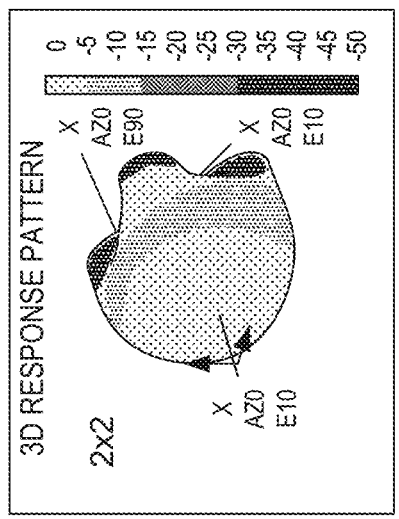
Figure 4D:
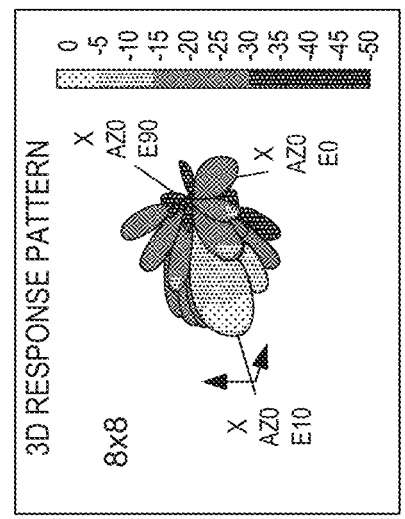

FIGS. 4A-4D are graphic visualizations of example radar radiation patterns radar signals in three-dimensional (3D) space. FIG. 4A shows a 3D radar radiation pattern for a 2×2 rectangle array of antennas. FIG. 4B shows a 3D radar radiation pattern for an 8×8 rectangle array of antennas. FIG. 4C shows a 3D radar radiation for a linear array with two antennas. FIG. 4D shows a 3D radar radiation for a linear array with eight antennas. FIG. 4B shows the radar radiation pattern for the antenna array with the highest resolution among the arrays shown I FIGS. 4A-4D.

Figure 5:
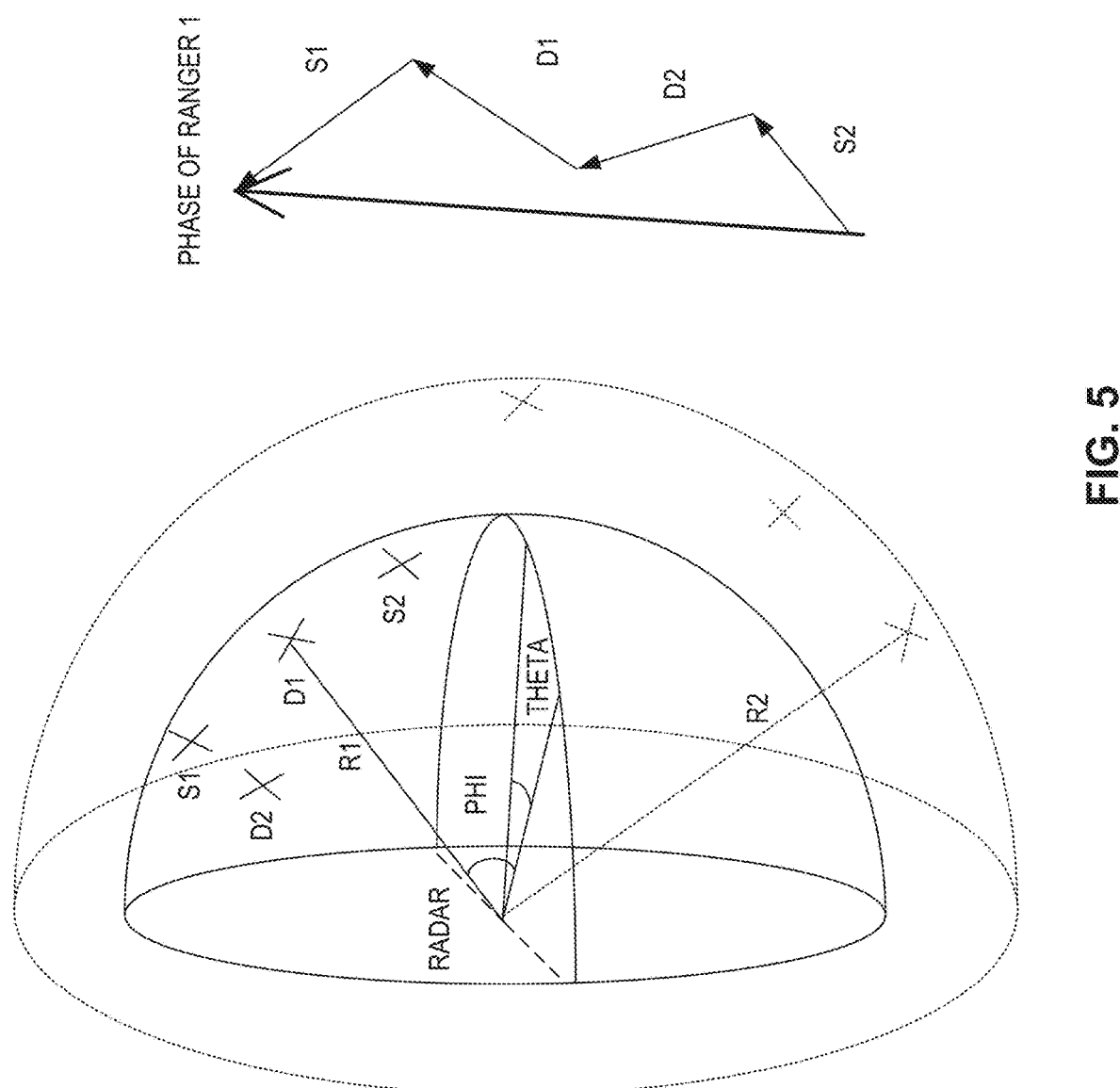
FIG. 5 is a graphic visualization of an example range-bin of radar signals in three-dimensional space.

FIG. 5 is a graphic visualization of an example range bin of radar signals in three-dimensional space. The example of FIG. 5 shows an ideal range-bin in which both the azimuth and the elevation angles are 180 degrees. In the example of FIG. 5, the FFT circuitry 216 implements range-FFT, which divides the ambient space, i.e., the environment 100 include onion-like layers. The width of the respective layers is based on the bandwidth of the radar signal. The layers represent different range-bins. The phase signal of a range-bin is a vector combination from all the objects, both static and dynamic, in the layer. Thus, the phase signal of a range-bin is impacted by different objects, both static and dynamic, located in the range-bin.

The bin selection circuitry 218 correlates the bins with the location data from the vision tracking system 202 to identify the bin that includes a peak which correlates to the location of the subject 104. With a bin identified that includes the location of the subject 104, the radar tracking system 204 can include, in some examples, a feedback loop for radar beamforming. With the beamforming, the radar steering circuitry 220 can steer the antenna array 212 or adjust the steering of the antenna array 212 to further focus on the location of the subject 104. In some examples, the steering of the antenna array 212 based on location data from the vision tracking system 202 is a coarse adjustment or steering of the antenna array 212. The steering of the antenna array 212 based on the feedback loop using the bin distance or location data from the radar tracking system 204 is a fine adjustment or steering of the antenna array 212.

When the antenna array 212 is steered to be focused on the location of interest—the location of the subject 104, the antenna array 212 captures less reflected signals from objects that are not of interest. In other words, signals from some directions are suppressed, and there is an enhanced read from the location of the subject 104. Radar can be considerably noisy, and these techniques suppress the noise and enhance the signal-to-noise ratio. The noise suppression also removes ghost effect from the received reflected radar signals. The image from the camera 206 may also be used to eliminate ghost effect because the image from the camera 206 can be used by the non-contact vital signs sensing circuitry 200 to confirm if a perceived object in the reflected radar signals is an actual object in the environment 100 or ghost effect noise.

The antennas 300 of the antenna array 212 selected based on the steering of the antenna array 212 emit radar into the environment 100. The reflected radar signals that are derived from the radar signals that hit the subject 104 and reflect back are received by the antennas 300 and communicated to the transceiver(s) 219. The vital signs extraction circuitry 222 extracts, detects, senses, measures, and/or calculates one or more vital signs of the subject 104 based on the reflected radar signal. In some examples, the signals undergo signal processing including, for example, amplification prior to extraction of the vital signs.

The vision tracking system 202 provides location and distance information. The radar tracking system corroborates distance information and also provides velocity or movement information. This information can be used to determined vital signs. For example, small surface movements of the chest of the subject 104 can be sensed or otherwise determined from the reflected radar signals. The signal power or amplitudes and frequency ranges of the reflected radar signals are different for different physiological measurements.

For example, a respiration rate produces larger movement in the chest than a heart rate, and these differences are reflected in the signal signatures. The chest surface moves predominantly due to inflation and deflation of the lungs during the breathing cycle. This movement ranges from about 4-12 millimeters (mm) with a frequency range of about 0.2-0.34 Hertz (Hz), which is about 12-20 breaths per minute. In addition to respiratory motion, the chest surface motion also includes comparatively faster but weaker vibrations, which is precordial motion, due to the beating of the heart. The chest surface motion due to the beating of the heart has an amplitude range of about 0.2-0.5 mm and frequency range of about 1-1.34 Hz, which is about 60-80 beats per minute (bpm). Thus, the vital signs extraction circuit 222 determines vital signs of the subject 104 based on the different amplitudes and frequency ranges included in the reflected radar signal.

When there are multiple subjects 104 in the environment 100, the subjects 104 may be monitored individually or one or more of the subjects 104 may be monitored simultaneously and/or intermittently. In some examples, the radar steering circuitry 220 steers the antenna array 212 in the location of a first subject 104, then adjusts the antenna array 212 to the location of the second subject 104, and then a third subject 104, etc. In some examples, the radar steering circuitry 220 steers the antenna array 212 back and forth between the locations of the subjects being monitored. In this example, the first subset of antennas 300 selected to focus on the first location is activated. Then the first subset of transceivers is deactivated and the second subset of antennas 300 selected to focus on the second location is activated. This sequence can be repeated multiple times. In addition, in some examples the first subset of antennas 300 and second subset of transceivers at least partially overlap. Also, in some examples, additional subsets of antennas 300 may be incorporated into rotation to monitoring additional subjects 104. Also, in some examples, the different subsets of antennas 300 designated to focus on respective locations in the environment 100 may be activated at different times and in different sequences such that data may be gathered from different subjects 104 at different times in no set order. In some examples, the antenna array 212 is steered such that the antenna array 212 transmits the radar beam to the locations of the multiple subjects 104 at the same time. The vital signs for the multiple subjects 104 can be determined and updated as the reflected radar signals are received.

The display overlay circuitry 224 can augment the image captured by the camera 206 or other rendering of the environment 100 and overlap or embed one or more of the vital signs on or in the image at or near the subject 104 or elsewhere in the image. FIG. 6 is an example in which an image of the subject 104 in the environment 100 in captured by the camera 206 and then rendered into an example stitched heat map 600. The beamforming occurs at different angles because of the relative positioning of the antennas 300. The received data at the different transceivers is combined and used to form the stitched heat map 600.

The vital signs of the subject 104 are overlayed in the heat map to produce the augmented display 602. In this example, the vital signs of the subject include a respiration or breathing rate (BR) or 0.5 HZ and a heart rate (HR) of 90 bpm. In other examples, the vital signs may appear towards one of the sides of the display or elsewhere in the augmented image. In an example with multiple subjects, the image may be augmented with multiple indicia of the vital signs specific to the different subjects 104. T The output display 226 presents the augmented display 602. The augmented display 602 provides a quick reference to the vital signs of the subject 104. The readily observable vital signs are useful for a caretaker to quickly assess a subject's health. In the illustrated example, the output display 226 is shown as part of the electronic device 102. In other examples, the output display 226 is on another electronic device. In some examples, the output display 226 is remotely connected to the electronic device 102. In some examples, the output display 226 is in a different physical location such as, for example, a health care setting remote from the environment 100, which is useful for telehealth scenarios.

In some examples, the non-contact vital signs sensing circuitry 200 determines if the subject is moving or still based on at least a subset of a plurality of images captured by the camera 206. The non-contact vital signs sensing circuitry 200 determines vital signs with a first accuracy when/if the subject 104 is moving between the first location and a second location in the environment (or among more locations within the environment). The non-contact vital signs sensing circuitry 200 determines vital signs with a second accuracy when/if the subject 104 is still (i.e., not physically moving about the environment). The second accuracy is greater than the first accuracy. In some examples, the non-contact vital signs sensing circuitry 200 generates a report associating a probability likelihood with the vital signs based on the first accuracy or the second accuracy. A higher probability likelihood is associated with a greater accuracy. Thus, the vision tracking system 202 assist to optimize the radar beamforming of the radar tracking system 204 and the vital signs measurements.

FIG. 2 is a of a block diagram of an example implementation of the non-contact vital signs sensing circuitry 200 to determine one or more vital signs of one or more subjects without physically contacting the subjects. The non-contact vital signs sensing circuitry of FIG. 2 may be instantiated (e.g., creating an instance of, bring into being for any length of time, materialize, implement, etc.) by processor circuitry such as a central processing unit executing instructions. Additionally or alternatively, the non-contact vital signs sensing circuitry of FIG. 2 may be instantiated (e.g., creating an instance of, bring into being for any length of time, materialize, implement, etc.) by an ASIC or an FPGA structured to perform operations corresponding to the instructions. It should be understood that some or all of the circuitry of FIG. 2 may, thus, be instantiated at the same or different times. Some or all of the circuitry may be instantiated, for example, in one or more threads executing concurrently on hardware and/or in series on hardware. Moreover, in some examples, some or all of the circuitry of FIG. 2 may be implemented by one or more virtual machines and/or containers executing on the microprocessor.

In some examples, the electronic device 102 includes means for capturing an image. For example, the means for capturing an image may be implemented by the camera 206.

In some examples, the electronic device 102 includes means for processing instructions. For example, the means for processing may be implemented by one or more of the non-contact vital signs circuitry 200, the subject detection circuitry 208, the location identification circuitry 210, the analog-to-digital converter 214, the FFT circuitry 216, the bin selection circuitry 218, the transceiver(s) 219, the radar steering circuitry 220, the vital signs extraction circuitry 222, and the display overlay circuitry 224. In some examples, one or more of the non-contact vital signs circuitry 200, the subject detection circuitry 208, the location identification circuitry 210, the analog-to-digital converter 214, the FFT circuitry 216, the bin selection circuitry 218, the transceiver(s) 219, the radar steering circuitry 220, the vital signs extraction circuitry 222, and the display overlay circuitry 224 may be instantiated by processor circuitry such as the example processor circuitry 812 of FIG. 8. For instance, the aforementioned circuitries 200, 208, 210, 214, 216, 218, 219, 220, 222, 224 may be instantiated by the example general purpose processor circuitry 900 of FIG. 9 executing machine executable instructions such as that implemented by the blocks of process 700 of FIG. 7. In some examples, the aforementioned circuitries 200, 208, 210, 214, 216, 218, 220, 219, 222, 224 may be instantiated by hardware logic circuitry, which may be implemented by an ASIC or the FPGA circuitry 1000 of FIG. 10 structured to perform operations corresponding to the machine readable instructions. Additionally or alternatively, the aforementioned circuitries 200, 208, 210, 214, 216, 218, 219, 220, 222, 224 may be instantiated by any other combination of hardware, software, and/or firmware. For example, the aforementioned circuitries 200, 208, 210, 214, 216, 218, 219, 220, 222, 224 may be implemented by at least one or more hardware circuits (e.g., processor circuitry, discrete and/or integrated analog and/or digital circuitry, an FPGA, an Application Specific Integrated Circuit (ASIC), a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the electronic device 102 includes means for presenting an augmented image. For example, the means for presenting may be implemented by the output display 226.

While an example manner of implementing the electronic device 102 of FIG. 1 is illustrated in FIG. 2, one or more of the elements, processes, and/or devices illustrated in FIG. 2 may be combined, divided, re-arranged, omitted, eliminated, and/or implemented in any other way. Further, the example subject detection circuitry 208, the example location identification circuitry 210, the example analog-to-digital converter 214, the example FFT circuitry 216, the example bin selection circuitry 218, the example transceiver(s) 219, the example radar steering circuitry 220, the example vital signs extraction circuitry 222, the example display overlay circuitry 224, and/or, more generally, the example non-contact vital signs sensing circuitry 200 of FIG. 2, may be implemented by hardware alone or by hardware in combination with software and/or firmware. Thus, for example, any of the example subject detection circuitry 208, the example location identification circuitry 210, the example analog-to-digital converter 214, the example FFT circuitry 216, the example bin selection circuitry 218, the example transceiver(s) 219, the example radar steering circuitry 220, the example vital signs extraction circuitry 222, the example display overlay circuitry 224, and/or, more generally, the example non-contact vital signs sensing circuitry 200 of FIG. 2, could be implemented by processor circuitry, analog circuit(s), digital circuit(s), logic circuit(s), programmable processor(s), programmable microcontroller(s), graphics processing unit(s) (GPU(s)), digital signal processor(s) (DSP(s)), application specific integrated circuit(s) (ASIC(s)), programmable logic device(s) (PLD(s)), and/or field programmable logic device(s) (FPLD(s)) such as Field Programmable Gate Arrays (FPGAs). Further still, the example non-contact vital signs sensing circuitry 200 of FIG. 2 may include one or more elements, processes, and/or devices in addition to, or instead of, those illustrated in FIG. 2, and/or may include more than one of any or all of the illustrated elements, processes and devices.

Figure 7:
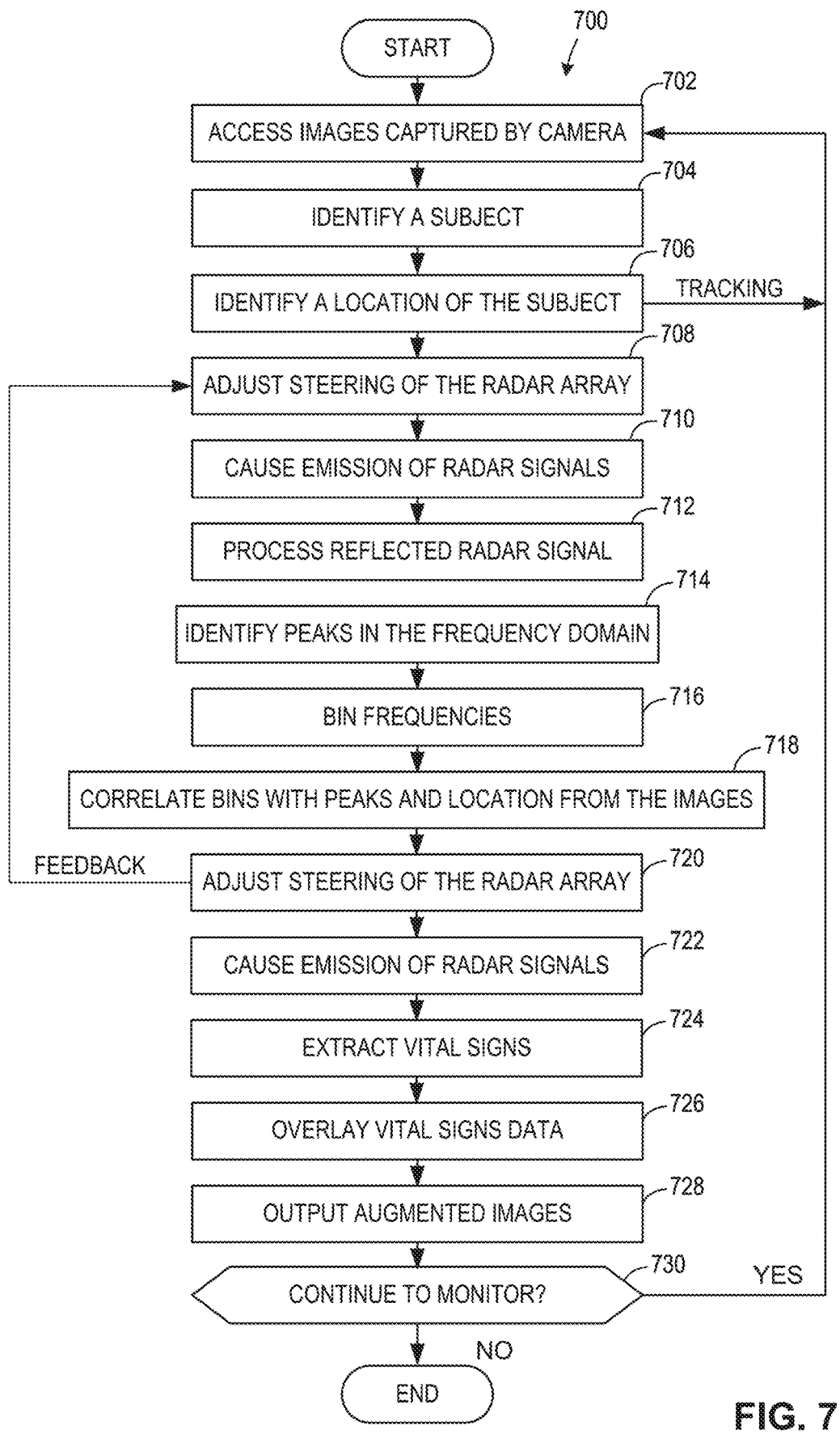
FIG. 7 is a flowchart representative of example machine readable instructions and/or example operations that may be executed by example processor circuitry to implement the non-contact vital sensing circuitry of FIG. 2.

A flowchart representative of example hardware logic circuitry, machine readable instructions, hardware implemented state machines, and/or any combination thereof for implementing the non-contact vital signs sensing circuitry 200 of FIG. 2 is shown in FIG. 7. The machine readable instructions may be one or more executable programs or portion(s) of an executable program for execution by processor circuitry, such as the processor circuitry 812 shown in the example processor platform 800 discussed below in connection with FIG. 8 and/or the example processor circuitry discussed below in connection with FIGS. 9 and/or 10. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowchart illustrated in FIG. 7, many other methods of implementing the example non-contact vital signs sensing circuitry 200 may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU), etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., as portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of machine executable instructions that implement one or more operations that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc., in order to execute the machine readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example operations of FIG. 7 may be implemented using executable instructions (e.g., computer and/or machine readable instructions) stored on one or more non-transitory computer and/or machine readable media such as optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms non-transitory computer readable medium and non-transitory computer readable storage medium are expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements or method actions may be implemented by, e.g., the same entity or object. Additionally, although individual features may be included in different examples or claims, these may possibly be combined, and the inclusion in different examples or claims does not imply that a combination of features is not feasible and/or advantageous.

FIG. 7 is a flowchart representative of example machine readable instructions and/or example operations 700 that may be executed and/or instantiated by processor circuitry to perform non-contact sensing of vital signs. The machine readable instructions and/or the operations 700 of FIG. 7 include the non-contact vital signs sensing circuitry 200 accessing one or more images captured by the camera 206 (block 702). The subject detection circuitry 208 identifies a subject or multiple subjects (e.g., the subjects 104) in an environment (e.g., the environment 100) shown in the images (block 704). The subject may be identified in accordance with the teachings disclosed above. The location identification circuitry 210 identifies a location of the subject in the environment (block 706). The location may be identified in accordance with the teachings disclosed above.

The non-contact vital signs sensing circuitry 200 may perform tracking of the subject in the environment for example as the subject moves about the environment, which would cause the locations of the subject to change. Thus, the example process 700 includes a tracking loop in which control of the process 700 continues with the non-contact vital signs sensing circuitry 200 accesses images of from the camera 702 to stay abreast of the identification of the subject and the locations of the subject in the environment.

The radar steering circuitry 220 uses the information from the analysis of the images from the camera, i.e., the identification of the subject and the location of the subject to adjust steering of the radar array (e.g., the antenna array 212) to focus the radar signal to the location of the subject (block 708). The transceiver(s) 219 of the non-contact vital signs sensing circuitry 200 causes emission of radar signal for example by energizing or otherwise causing transmission of radar signals from the antennas 300 and, in particular, from a subset of the antennas 300 that would direct the radar signals toward the location of the subject (block 710). The emitted radar signals reflect off objects in the environment including the subject. The reflected radar signals are received by one or more of the antennas 300 at the antenna array 212.

Elements of the radar tracking system 204 including, for example, the analog-to-digital converter 214, the FFT circuitry 216, the bin selection circuitry 218, and the transceiver(s) 219 process the reflected radar signals (block 712). Signal processing includes filtering, noise reduction, amplification, conversion of analog signals to digital signals, and other processing disclosed herein. The FFT circuitry 216 identifies peaks in the reflected radar signals (block 714). The bin selection circuitry 218 bins the frequencies (block 716). The bin selection circuitry 218 correlates the bins that peaks with the location information of the subject 104 from the images of the camera 206 (block 718). The bins represent distances, and the bin with a peak that matches the location of the subject becomes the bin of interest.

Based on identification of the bin of interest, the radar steering circuitry 220 adjusts the steering of the antenna array 212 of the radar toward to focus further on the subject 104 (block 720). The radar tracking system 204 includes a feedback protocol in which information related to the tuning or steering of the antenna array 212 based on identification of the bin of interest is used to validate the initial steering of the antenna array 212 based on the location of the subject 104 using data from the image captured by the camera 206. A machine learning process also may be invoked so that the non-contact vital signs sensing circuitry 200 learns more accurate steering based on the location of the subject. The feedback loop provides information to the radar steering circuitry 220 for processing at block 708.

After the radar steering circuitry 220 adjusts the steering of the antenna array 212 of the radar toward to focus further on the subject 104 based on identification of the bin of interest (block 720), the transceiver(s) 219 causes emission of radar signal for example by energizing and/or otherwise causing transmission of radar signals from the antennas 300 and, in particular, from a subset of the antennas 300 that would direct the radar signals toward the location of the subject (block 722). In some examples, the emission of radar signals at block 710 is continuous or otherwise ongoing and the separate emission at block 722 is not an extra step.

The emitted radar signals reflect off objects in the environment including the subject and specifically the subject's chest. The reflected radar signals are received by one or more of the antennas 300 at the antenna array 212. The vital signs extraction circuitry 222 extracts one or more vital signs from the subject (block 724). The vital signs may be extracted, measured, determined, calculated, sensed, etc. in any many disclosed above.

The display overlay circuitry 224 overlays vital signs data on the image captured by the camera 206 or an image derived therefrom (block 726). The non-contact vital signs circuitry 200 outputs the augmented images for display by, for example, the output display 226 (block 728). The non-contact vital signs circuitry 200 determines if further monitoring of the subjects is to occur (block 730). When the non-contact vital signs circuitry 200 determines that further monitoring of the subjects is to occur (block 730: YES), the example process 700 continues with the non-contact vital signs sensing circuitry 200 accesses images of from the camera 702. When the non-contact vital signs circuitry 200 determines that no further monitoring of the subjects is to occur (block 730: NO), the process 700 ends.

FIG. 800 is a block diagram of an example processor platform 800 structured to execute and/or instantiate the machine readable instructions and/or the operations of FIG. 7 to implement the non-contact vital signs circuitry 200 of FIG. 2. The processor platform 800 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset (e.g., an augmented reality (AR) headset, a virtual reality (VR) headset, etc.) or other wearable device, or any other type of computing device.

The processor platform 800 of the illustrated example includes processor circuitry 812. The processor circuitry 812 of the illustrated example is hardware. For example, the processor circuitry 812 can be implemented by one or more integrated circuits, logic circuits, FPGAs, microprocessors, CPUs, GPUs, DSPs, and/or microcontrollers from any desired family or manufacturer. The processor circuitry 812 may be implemented by one or more semiconductor based (e.g., silicon based) devices. In this example, the processor circuitry 812 implements the non-contact vital signs circuitry 200, the vision tracking system 202, the radar tracking system 204, the subject detection circuitry 208, the location identification circuitry 210, the analog-to-digital converter 214, the FFT circuitry 216, the bin selection circuitry 218, the transceiver(s) 219, the radar steering circuitry 220, the vital signs extraction circuitry 222, and the display overlay circuitry 224.

The processor circuitry 812 of the illustrated example includes a local memory 813 (e.g., a cache, registers, etc.). The processor circuitry 812 of the illustrated example is in communication with a main memory including a volatile memory 814 and a non-volatile memory 816 by a bus 818. The volatile memory 814 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 816 may be implemented by flash memory and/or any other desired type of memory device. Access to the main memory 814, 816 of the illustrated example is controlled by a memory controller 817.

The processor platform 800 of the illustrated example also includes interface circuitry 820. The interface circuitry 820 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 822 are connected to the interface circuitry 820. The input device(s) 822 permit(s) a user to enter data and/or commands into the processor circuitry 812. The input device(s) 822 can be implemented by, for example, an audio sensor, a microphone, a camera (still or video), a keyboard, a button, a mouse, a touchscreen, a track-pad, a trackball, an isopoint device, and/or a voice recognition system.

One or more output devices 824 are also connected to the interface circuitry 820 of the illustrated example. The output device(s) 824 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 820 of the illustrated example, thus, typically includes a graphics driver card, a graphics driver chip, and/or graphics processor circuitry such as a GPU.

The interface circuitry 820 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 826. The communication can be by, for example, an Ethernet connection, a digital subscriber line (DSL) connection, a telephone line connection, a coaxial cable system, a satellite system, a line-of-site wireless system, a cellular telephone system, an optical connection, etc.

The processor platform 800 of the illustrated example also includes one or more mass storage devices 828 to store software and/or data. Examples of such mass storage devices 828 include magnetic storage devices, optical storage devices, floppy disk drives, HDDs, CDs, Blu-ray disk drives, redundant array of independent disks (RAID) systems, solid state storage devices such as flash memory devices and/or SSDs, and DVD drives.

The machine executable instructions 832, which may be implemented by the machine readable instructions of FIG. 7, may be stored in the mass storage device 828, in the volatile memory 814, in the non-volatile memory 816, and/or on a removable non-transitory computer readable storage medium such as a CD or DVD.

Figure 8:
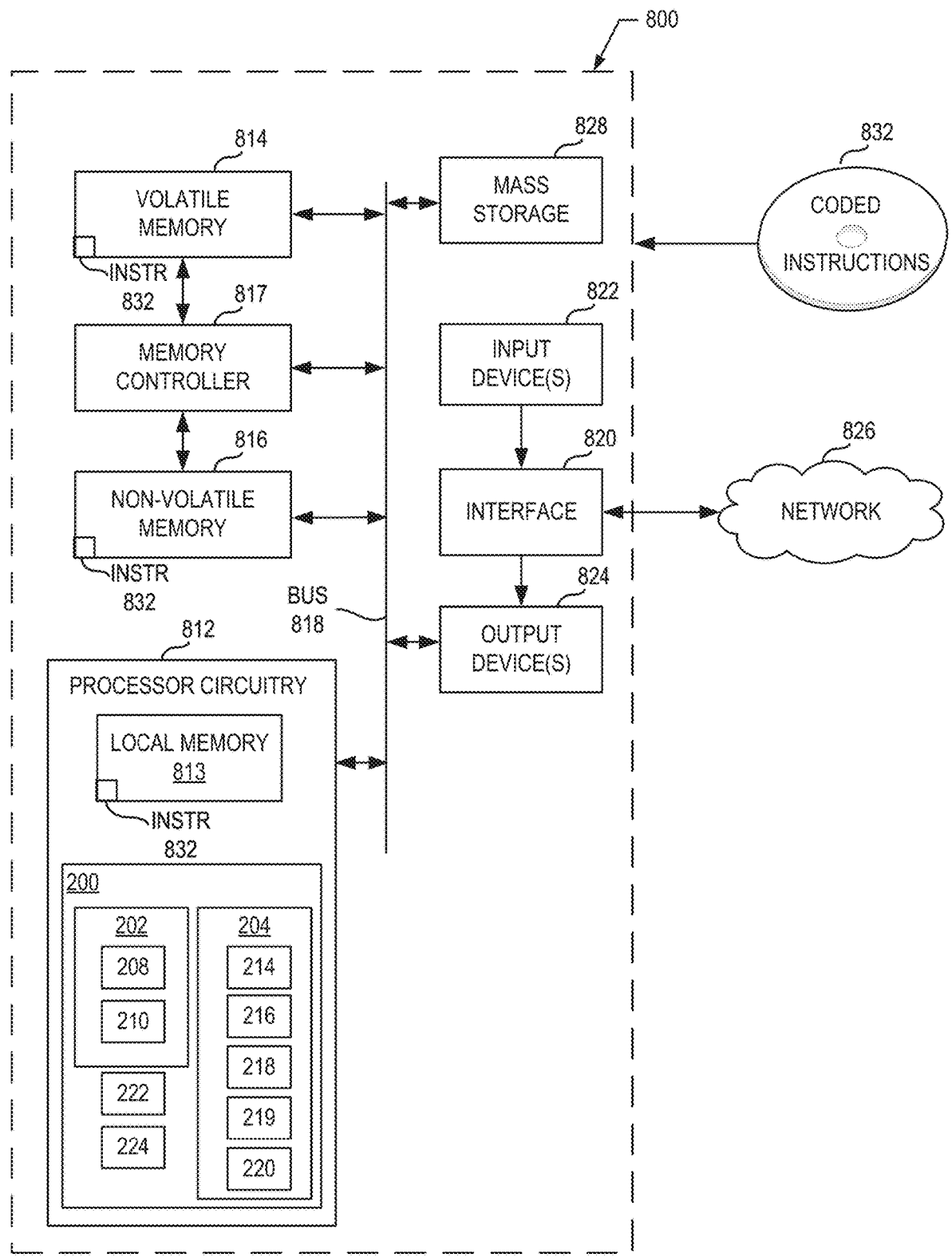
FIG. 8 is a block diagram of an example processing platform including processor circuitry structured to execute the example machine readable instructions and/or the example operations of FIG. 7 to implement the non-contact vital sensing circuitry of FIG. 2.
Figure 9:
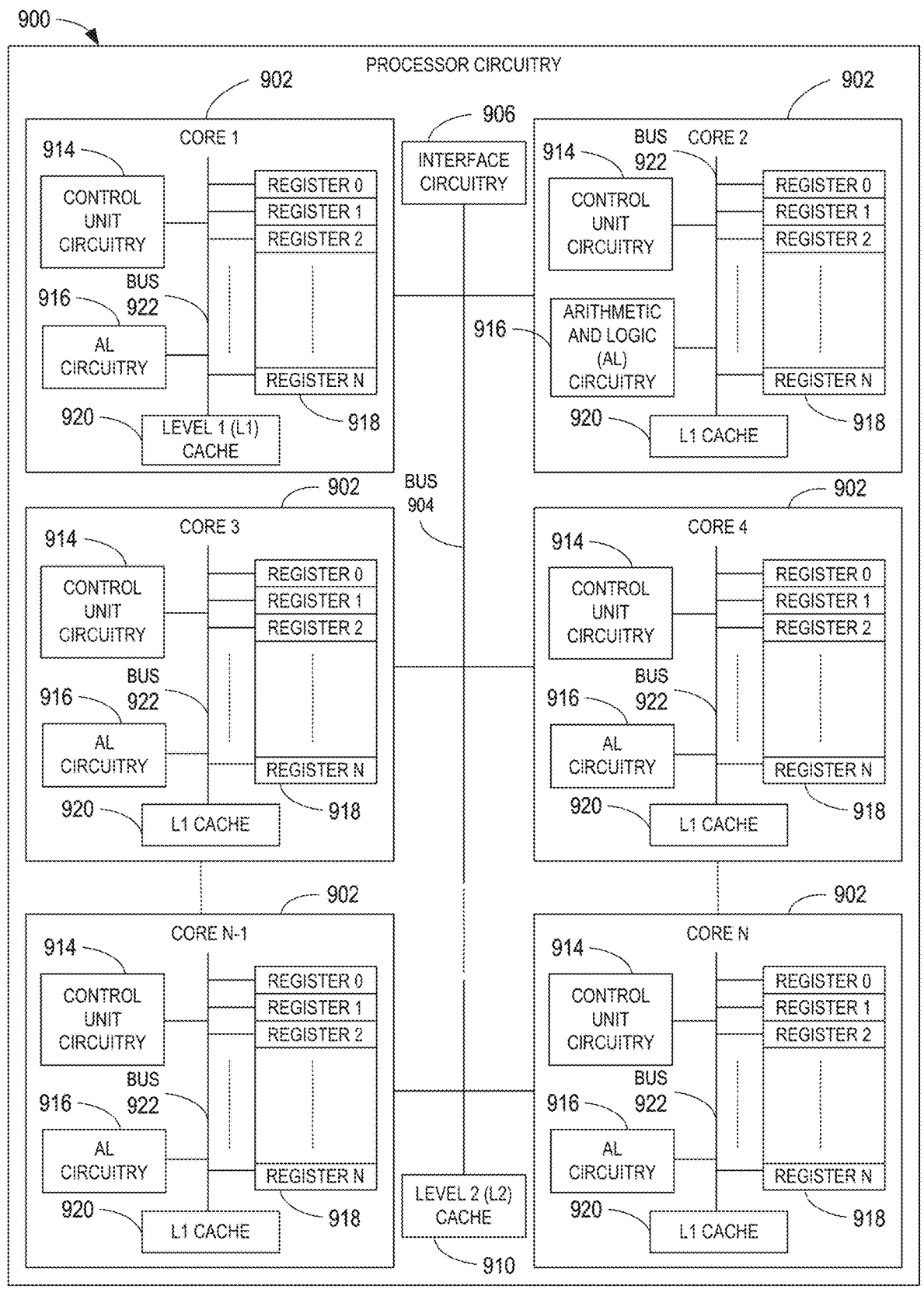
FIG. 9 is a block diagram of an example implementation of the processor circuitry of FIG. 8.

FIG. 9 is a block diagram of an example implementation of the processor circuitry 812 of FIG. 8. In this example, the processor circuitry 812 of FIG. 8 is implemented by a general purpose microprocessor 900. The general purpose microprocessor circuitry 900 executes some or all of the machine readable instructions of the flowchart of FIG. 7 to effectively instantiate the circuitry of FIG. 2 as logic circuits to perform the operations corresponding to those machine readable instructions. In some such examples, the circuitry of FIG. 2 is instantiated by the hardware circuits of the microprocessor 900 in combination with the instructions. For example, the microprocessor 900 may implement multi-core hardware circuitry such as a CPU, a DSP, a GPU, an XPU, etc. Although it may include any number of example cores 902 (e.g., 1 core), the microprocessor 900 of this example is a multi-core semiconductor device including N cores. The cores 902 of the microprocessor 900 may operate independently or may cooperate to execute machine readable instructions. For example, machine code corresponding to a firmware program, an embedded software program, or a software program may be executed by one of the cores 902 or may be executed by multiple ones of the cores 902 at the same or different times. In some examples, the machine code corresponding to the firmware program, the embedded software program, or the software program is split into threads and executed in parallel by two or more of the cores 902. The software program may correspond to a portion or all of the machine readable instructions and/or operations represented by the flowchart of FIG. 7.

The cores 902 may communicate by a first example bus 904. In some examples, the first bus 904 may implement a communication bus to effectuate communication associated with one(s) of the cores 902. For example, the first bus 904 may implement at least one of an Inter-Integrated Circuit (I2C) bus, a Serial Peripheral Interface (SPI) bus, a PCI bus, or a PCIe bus. Additionally or alternatively, the first bus 904 may implement any other type of computing or electrical bus. The cores 902 may obtain data, instructions, and/or signals from one or more external devices by example interface circuitry 906. The cores 902 may output data, instructions, and/or signals to the one or more external devices by the interface circuitry 906. Although the cores 902 of this example include example local memory 920 (e.g., Level 1 (L1) cache that may be split into an L1 data cache and an L1 instruction cache), the microprocessor 900 also includes example shared memory 910 that may be shared by the cores (e.g., Level 2 (L2_cache)) for high-speed access to data and/or instructions. Data and/or instructions may be transferred (e.g., shared) by writing to and/or reading from the shared memory 910. The local memory 920 of each of the cores 902 and the shared memory 910 may be part of a hierarchy of storage devices including multiple levels of cache memory and the main memory (e.g., the main memory 814, 816 of FIG. 8). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 902 may be referred to as a CPU, DSP, GPU, etc., or any other type of hardware circuitry. Each core 902 includes control unit circuitry 914, arithmetic and logic (AL) circuitry (sometimes referred to as an ALU) 916, a plurality of registers 918, the L1 cache 920, and a second example bus 922. Other structures may be present. For example, each core 902 may include vector unit circuitry, single instruction multiple data (SIMD) unit circuitry, load/store unit (LSU) circuitry, branch/jump unit circuitry, floating-point unit (FPU) circuitry, etc. The control unit circuitry 914 includes semiconductor-based circuits structured to control (e.g., coordinate) data movement within the corresponding core 902. The AL circuitry 916 includes semiconductor-based circuits structured to perform one or more mathematic and/or logic operations on the data within the corresponding core 902. The AL circuitry 916 of some examples performs integer based operations. In other examples, the AL circuitry 916 also performs floating point operations. In yet other examples, the AL circuitry 916 may include first AL circuitry that performs integer based operations and second AL circuitry that performs floating point operations. In some examples, the AL circuitry 916 may be referred to as an Arithmetic Logic Unit (ALU). The registers 918 are semiconductor-based structures to store data and/or instructions such as results of one or more of the operations performed by the AL circuitry 916 of the corresponding core 902. For example, the registers 918 may include vector register(s), SIMD register(s), general purpose register(s), flag register(s), segment register(s), machine specific register(s), instruction pointer register(s), control register(s), debug register(s), memory management register(s), machine check register(s), etc. The registers 918 may be arranged in a bank as shown in FIG. 9. Alternatively, the registers 918 may be organized in any other arrangement, format, or structure including distributed throughout the core 902 to shorten access time. The second bus 922 may implement at least one of an I2C bus, a SPI bus, a PCI bus, or a PCIe bus Each core 902 and/or, more generally, the microprocessor 900 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 900 is a semiconductor device fabricated to include many transistors interconnected to implement the structures described above in one or more integrated circuits (ICs) contained in one or more packages. The processor circuitry may include and/or cooperate with one or more accelerators. In some examples, accelerators are implemented by logic circuitry to perform certain tasks more quickly and/or efficiently than can be done by a general purpose processor. Examples of accelerators include ASICs and FPGAs such as those discussed herein. A GPU or other programmable device can also be an accelerator. Accelerators may be on-board the processor circuitry, in the same chip package as the processor circuitry and/or in one or more separate packages from the processor circuitry.

FIG. 6 is a block diagram of another example implementation of the processor circuitry 812 of FIG. 8. In this example, the processor circuitry 812 is implemented by FPGA circuitry 900. The FPGA circuitry 900 can be used, for example, to perform operations that could otherwise be performed by the example microprocessor 900 of FIG. 9 executing corresponding machine readable instructions. However, once configured, the FPGA circuitry 900 instantiates the machine readable instructions in hardware and, thus, can often execute the operations faster than they could be performed by a general purpose microprocessor executing the corresponding software.

Figure 10:
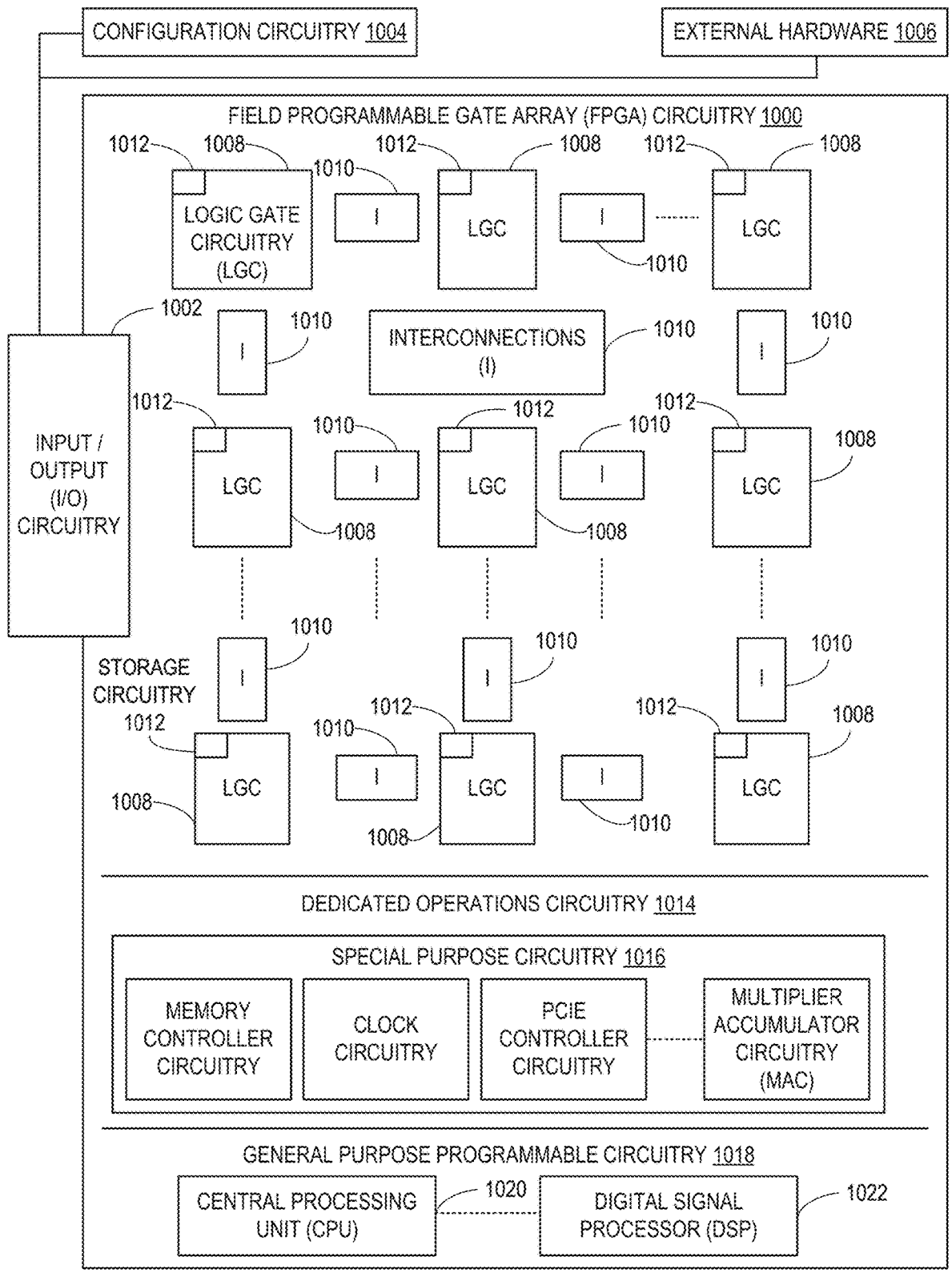
FIG. 10 is a block diagram of another example implementation of the processor circuitry of FIG. 8.

More specifically, in contrast to the microprocessor 900 of FIG. 9 described above (which is a general purpose device that may be programmed to execute some or all of the machine readable instructions represented by the flowchart of FIG. 7 but whose interconnections and logic circuitry are fixed once fabricated), the FPGA circuitry 1000 of the example of FIG. 10 includes interconnections and logic circuitry that may be configured and/or interconnected in different ways after fabrication to instantiate, for example, some or all of the machine readable instructions represented by the flowchart of FIG. 8. In particular, the FPGA 1000 may be thought of as an array of logic gates, interconnections, and switches. The switches can be programmed to change how the logic gates are interconnected by the interconnections, effectively forming one or more dedicated logic circuits (unless and until the FPGA circuitry 1000 is reprogrammed). The configured logic circuits enable the logic gates to cooperate in different ways to perform different operations on data received by input circuitry. Those operations may correspond to some or all of the software represented by the flowchart of FIG. 7. As such, the FPGA circuitry 1000 may be structured to effectively instantiate some or all of the machine readable instructions of the flowchart of FIG. 7 as dedicated logic circuits to perform the operations corresponding to those software instructions in a dedicated manner analogous to an ASIC. Therefore, the FPGA circuitry 1000 may perform the operations corresponding to the some or all of the machine readable instructions of FIG. 7 faster than the general purpose microprocessor can execute the same.

In the example of FIG. 10, the FPGA circuitry 1000 is structured to be programmed (and/or reprogrammed one or more times) by an end user by a hardware description language (HDL) such as Verilog. The FPGA circuitry 1000 of FIG. 6, includes example input/output (I/O) circuitry 1002 to obtain and/or output data to/from example configuration circuitry 1004 and/or external hardware (e.g., external hardware circuitry) 1006. For example, the configuration circuitry 1004 may implement interface circuitry that may obtain machine readable instructions to configure the FPGA circuitry 1000, or portion(s) thereof. In some such examples, the configuration circuitry 1004 may obtain the machine readable instructions from a user, a machine (e.g., hardware circuitry (e.g., programmed or dedicated circuitry) that may implement an Artificial Intelligence/Machine Learning (AI/ML) model to generate the instructions), etc. In some examples, the external hardware 1006 may implement the microprocessor 900 of FIG. 9. The FPGA circuitry 1000 also includes an array of example logic gate circuitry 1008, a plurality of example configurable interconnections 1010, and example storage circuitry 1012. The logic gate circuitry 1008 and interconnections 1010 are configurable to instantiate one or more operations that may correspond to at least some of the machine readable instructions of FIG. 7 and/or other desired operations. The logic gate circuitry 1008 shown in FIG. 10 is fabricated in groups or blocks. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 1008 to enable configuration of the electrical structures and/or the logic gates to form circuits to perform desired operations. The logic gate circuitry 1008 may include other electrical structures such as look-up tables (LUTs), registers (e.g., flip-flops or latches), multiplexers, etc.

The interconnections 1010 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 1008 to program desired logic circuits.

The storage circuitry 1012 of the illustrated example is structured to store result(s) of the one or more of the operations performed by corresponding logic gates. The storage circuitry 1012 may be implemented by registers or the like. In the illustrated example, the storage circuitry 1012 is distributed amongst the logic gate circuitry 1008 to facilitate access and increase execution speed.

The example FPGA circuitry 1000 of FIG. 10 also includes example Dedicated Operations Circuitry 1014. In this example, the Dedicated Operations Circuitry 1014 includes special purpose circuitry 1016 that may be invoked to implement commonly used functions to avoid the need to program those functions in the field. Examples of such special purpose circuitry 1016 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 1000 may also include example general purpose programmable circuitry 1018 such as an example CPU 1020 and/or an example DSP 1022. Other general purpose programmable circuitry 1018 may additionally or alternatively be present such as a GPU, an XPU, etc., that can be programmed to perform other operations.

Although FIGS. 9 and 10 illustrate two example implementations of the processor circuitry 812 of FIG. 8, many other approaches are contemplated. For example, as mentioned above, modern FPGA circuitry may include an onboard CPU, such as one or more of the example CPU 1020 of FIG. 10. Therefore, the processor circuitry 812 of FIG. 8 may additionally be implemented by combining the example microprocessor 900 of FIG. 9 and the example FPGA circuitry 1000 of FIG. 10. In some such hybrid examples, a first portion of the machine readable instructions represented by the flowchart of FIG. 7 may be executed by one or more of the cores 902 of FIG. 9, a second portion of the machine readable instructions represented by the flowchart of FIG. 7 may be executed by the FPGA circuitry 1000 of FIG. 10, and/or a third portion of the machine readable instructions represented by the flowchart of FIG. 7 may be executed by an ASIC. It should be understood that some or all of the circuitry of FIG. 2 may, thus, be instantiated at the same or different times. Some or all of the circuitry may be instantiated, for example, in one or more threads executing concurrently and/or in series. Moreover, in some examples, some or all of the circuitry of FIG. 2 may be implemented within one or more virtual machines and/or containers executing on the microprocessor.

In some examples, the processor circuitry 812 of FIG. 8 may be in one or more packages. For example, the processor circuitry 900 of FIG. 9 and/or the FPGA circuitry 1000 of FIG. 10 may be in one or more packages. In some examples, an XPU may be implemented by the processor circuitry 812 of FIG. 8, which may be in one or more packages. For example, the XPU may include a CPU in one package, a DSP in another package, a GPU in yet another package, and an FPGA in still yet another package.

Figure 11:
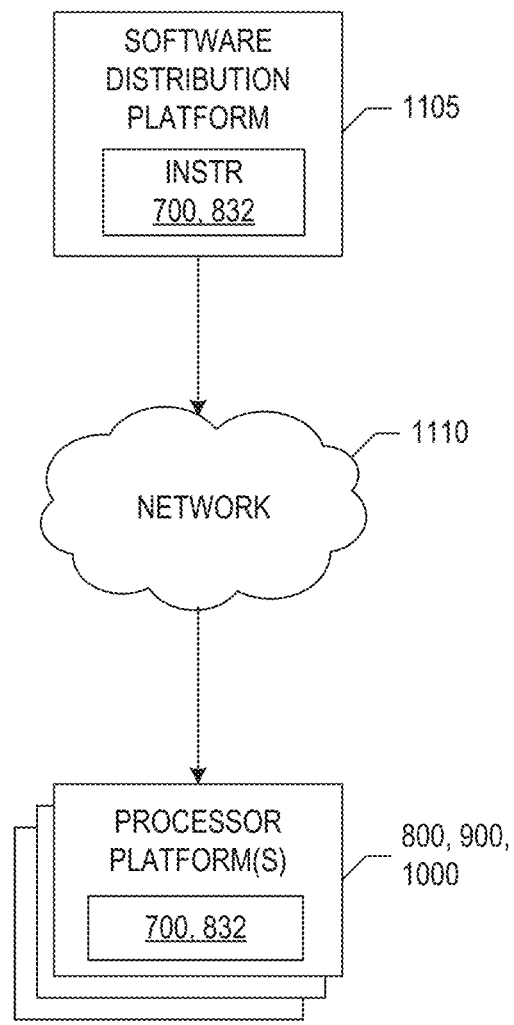
FIG. 11 is a block diagram of an example software distribution platform (e.g., one or more servers) to distribute software (e.g., software corresponding to the example machine readable instructions of FIG. 7) to client devices associated with end users and/or consumers (e.g., for license, sale, and/or use), retailers (e.g., for sale, re-sale, license, and/or sub-license), and/or original equipment manufacturers (OEMs) (e.g., for inclusion in products to be distributed to, for example, retailers and/or to other end users such as direct buy customers).

A block diagram illustrating an example software distribution platform 1105 to distribute software such as the example machine readable instructions 700 of FIG. 7 and 832 of FIG. 8 to hardware devices owned and/or operated by third parties is illustrated in FIG. 11. The example software distribution platform 1105 may be implemented by any computer server, data facility, cloud service, etc., capable of storing and transmitting software to other computing devices. The third parties may be customers of the entity owning and/or operating the software distribution platform 1105. For example, the entity that owns and/or operates the software distribution platform 1105 may be a developer, a seller, and/or a licensor of software such as the example machine readable instructions 832 of FIG. 8. The third parties may be consumers, users, retailers, OEMs, etc., who purchase and/or license the software for use and/or re-sale and/or sub-licensing. In the illustrated example, the software distribution platform 1105 includes one or more servers and one or more storage devices. The storage devices store the machine readable instructions 832, which may correspond to the example machine readable instructions 700 of FIG. 7 as described above. The one or more servers of the example software distribution platform 1105 are in communication with a network 1110, which may correspond to any one or more of the Internet and/or any of the example networks described above. In some examples, the one or more servers are responsive to requests to transmit the software to a requesting party as part of a commercial transaction. Payment for the delivery, sale, and/or license of the software may be handled by the one or more servers of the software distribution platform and/or by a third party payment entity. The servers enable purchasers and/or licensors to download the machine readable instructions 832 from the software distribution platform 1105. For example, the software, which may correspond to the example machine readable instructions 700 of FIG. 7, may be downloaded to the example processor platform 800, which is to execute the machine readable instructions 832 to implement the non-contact vital signs sensing circuitry 200. In some example, one or more servers of the software distribution platform 1105 periodically offer, transmit, and/or force updates to the software (e.g., the example machine readable instructions 832 of FIG. 8) to ensure improvements, patches, updates, etc., are distributed and applied to the software at the end user devices.

From the foregoing, it will be appreciated that example systems, methods, apparatus, systems, and articles of manufacture have been disclosed that enable non-contact sensing of vital signs. Disclosed systems, methods, apparatus, and articles of manufacture improve the efficiency of using a computing device by enabling the device to more accurately focus or steer an antenna array transmitting radar signals toward a chest of a subject to gather data indicative of vital signs. Disclosed systems, methods, apparatus, and articles of manufacture are accordingly directed to one or more improvement(s) in the operation of a machine such as a computer or other electronic and/or mechanical device.

The examples disclosed herein combine vision data with radar data that allows for adaptive beamforming for steering a radar antenna array for non-contact vital signs extraction from a subject despite movement of the subject throughout an environment. Using the subject location and movement across the environment with a vision system along with radar beamforming outputs to steer the transmission azimuth and elevation of the radar maintains maximum transmission power over the chest area of the subject.

The combination of vision data and radar data enhances the capabilities of the examples disclosed here because more information can be gathered and verified including, for example, distance, tracking, angular velocity, linear velocity, mobility, and vital signs. Corroboration or validation between the vision system data and the radar system data also can reduce ghost effect and occlusions in the environment. Occlusions can be accounted for because with the vision data and radar data, the examples disclosed herein can identify the same subject moving around in the environment with occlusions and re-attach vital sign information to the same subject in the augmented image. The combination of vision data and radar data can be used to classify human activity to filter out doppler changes due to random body movement.

The example non-contact vital signs measurement features disclosed herein may be used ambiently to gather vital signs without disrupting or contacting the subject. The vital signs can be measured long term including, for example, twenty-four hours per day. The examples disclosed herein can be implemented in dedicated, stand along devices, incorporated into laptops and other computing devices, and/or leverage processing capabilities in edge platforms. The example disclosed herein may be used to detect a range of physiological activity including, for example, vital signs measurements, physical and mobility progress monitoring at different settings including for example homes and hospitals, daily activity classification for patients in different settings and/or for wellbeing initiatives at office spaces, and detection of deteriorating health patterns to enable action by care providers before a negative health scenario occurs.

Examples disclosed herein enable contactless human vital detection using radar data and visual data, for example, with a low resolution radar and an RGB camera. In some examples, the RGB camera detects, locates, and tracks a human, and the low-resolution radar measures vitals by focusing radar beam at the tracked target location. In some examples, a radar with sufficient range resolution and angle resolution also detects, locates, and tracks a human.

In some examples, the camera assists the radar on the angle resolution for performance of continuous and reliable beamforming. In some examples, both the radar and the camera are rigidly connected. Based on the pixel value of a human chest point, the camera can estimate both azimuth and elevation angles of the radar beam with good resolution. The radar can estimate the radial range towards the human chest. The steering of radar beam as disclosed in examples herein is used if/when the human moves or is moved out of the coverage of radar. Thus, in some examples, steering of the beam is not performed for angle accuracy but to ensure coverage of the subject.

Example methods, apparatus, systems, and articles of manufacture are disclosed for non-contact sensing of vital signs. Example 1 includes an electronic device to measure vital signs, the electronic device comprising: a camera to capture an image; a radar antenna to transmit and receive radar signals; and processor circuitry to: identify a subject in the image; identify a location of the subject in an environment; control the radar antenna to steer radar signals toward the location; and determine a vital sign of the subject based on a reflected radar signal.

Example 2 includes the electronic device of Example 1, wherein the processor circuitry is to augment the image with data indicative of the vital sign to create an augmented image.

Example 3 includes the electronic device of Examples 1 or 2, further including a display screen to present the augmented image.

Example 4 includes the electronic device of any of Examples 1-3, wherein the reflected radar signal is a first reflected radar signal, and the processor circuitry is to: process the first reflected radar signal and a second reflected radar signal to create a plurality of bins based on frequencies or phases of the reflected radar signals, the bins corresponding to respective locations in the environment; identify a peak in a bin of the plurality of bins, the peak indicative of a presence of the subject; perform a comparison of the location and the bin with the peak; and steer the radar signals based on the comparison.

Example 5 includes the electronic device of any of Examples 1-4, wherein the processor circuitry is to analyze phase information in the reflected radar signal to identify movements by the subject.

Example 6 includes the electronic device of any of Examples 1-5, wherein the vital sign is a first vital sign, and the processor circuitry is to: determine the first vital sign based on a first range of movement; and determine a second vital sign based on a second range of movement, the second range of movement different than the first range of movement.

Example 7 includes the electronic device of any of Examples 1-6, wherein the second range of movement is larger than the first range of movement, the first vital sign is a heart rate and the second vital sign is a respiratory rate.

Example 8 includes the electronic device of any of Examples 1-7, wherein the electronic device is physically distant from the subject.

Example 9 includes the electronic device of any of Examples 1-8, wherein the radar antenna includes an array of antennas and the processor circuitry is to steer the radar signal by energizing different subsets of the antennas used to transmit the radar signals.

Example 10 includes the electronic device of any of Examples 1-9, wherein the location is a first location and the radar antenna includes an array of antennas, and to steer the radar antenna, the processor circuitry is to: energize a first subset of the antennas when the subject is in the first location; and energize a second subset of the antennas when the subject is in a second location in the environment.

Example 11 includes the electronic device of any of Examples 1-10, wherein the subject is a first subject, the vital sign is a first vital sign, and the radar antenna includes an array of antennas, and to steer the radar antenna, the processor circuitry is to: energize a first subset of the antennas to measure the first vital sign of the first subject; and energize a second subset of the antennas to measure a second vital sign of a second subject.

Example 12 includes the electronic device of any of Examples 1-11, wherein the processor circuitry is to measure the first vital sign and the second vital while the first subject and the second subject are in the environment at the same time.

Example 13 includes electronic device of any of Examples 1-12, wherein the location is a first location, and the camera is to capture a plurality of images, and the processor circuitry is to: determine if the subject is moving or still based on at least a subset of the plurality of images; determine the vital sign with a first accuracy if the subject is moving between the first location and a second location in the environment, and determine the vital sign with a second accuracy if the subject is still, the second accuracy greater than the first accuracy; and generate a report associating a probability likelihood with the vital sign based on the first accuracy or the second accuracy.

Example 14 includes an electronic device to measure vital signs, the electronic device comprising: means for capturing an image; a radar antenna to transmit and receive radar signals; and means for processing instructions to: identify a subject in the image; identify a location of the subject in an environment; control the radar antenna to steer the radar signals toward the location; and determine a vital sign of the subject based on a reflected radar signal.

Example 15 includes the electronic device of Example 14, wherein the means for processing is to augment the image with data indicative of the vital sign to create an augmented image.

Example 16 includes the electronic device of Examples 14 or 15, further including means for presenting the augmented image.

Example 17 includes the electronic device of any of Examples 14-16, wherein the reflected radar signal is a first reflected radar signal, and the means for processing is to: process the first reflected radar signal and a second reflected radar signal to create a plurality of bins based on frequencies or phases of the reflected radar signals, the bins corresponding to respective locations in the environment; identify a peak in a bin of the plurality of bins, the peak indicative of a presence of the subject; perform a comparison of the location and the bin with the peak; and steer the radar signals based on the comparison.

Example 18 includes the electronic device of any of Examples 14-17, wherein the means for processing is to analyze phase information in the reflected radar signal to identify movements by the subject.

Example 19 includes the electronic device of any of Examples 14-18, wherein the vital sign is a first vital sign, and the means for processing is to: determine the first vital sign based on a first range of movement; and determine a second vital sign based on a second range of movement, the second range of movement different than the first range of movement.

Example 20 includes the electronic device of any of Examples 14-19, wherein the second range of movement is larger than the first range of movement, the first vital sign is a heart rate and the second vital sign is a respiratory rate.

Example 21 includes the electronic device of any of Examples 14-20, wherein the electronic device is physically distant from the subject.

Example 22 includes the electronic device of any of Examples 14-21, wherein the radar antenna includes an array of antennas and the means for processing is to steer the radar signal by energizing different subsets of the antennas used to transmit the radar signals.

Example 23 includes the electronic device of any of Examples 14-22, wherein the location is a first location and the radar antenna includes an array of antennas, and to steer the radar antenna, the means for process is to: energize a first subset of the antennas when the subject is in the first location; and energize a second subset of the antennas when the subject is in a second location in the environment.

Example 24 includes the electronic device of any of Examples 14-23, wherein the subject is a first subject, the vital sign is a first vital sign, and the radar antenna includes an array of antennas, and to steer the radar antenna, the means for processing is to: energize a first subset of the antennas to measure the first vital sign of the first subject; and energize a second subset of the antennas to measure a second vital sign of a second subject.

Example 25 includes the electronic device of any of Examples 14-24, wherein the means for processing is to measure the first vital sign and the second vital while the first subject and the second subject are in the environment at the same time.

Example 26 includes a non-transitory computer readable medium comprising instructions that, when executed, cause one or more processors to at least: identify a subject in an image; identify a location of the subject in an environment of the image; control the radar antenna to steer the radar signals toward the location; and determine a vital sign of the subject based on a reflected radar signal.

Example 27 includes the computer readable medium of Example 26, wherein the instructions, when executed, cause the one or more processors to augment the image with data indicative of the vital sign to create an augmented image.

Example 28 includes the computer readable medium of Examples 26 or 27, wherein the instructions, when executed, cause the one or more processors to output the augmented image to a display device.

Example 29 includes the computer readable medium of any of Examples 26-28, wherein the reflected radar signal is a first reflected radar signal, and the instructions, when executed, cause the one or more processors to: process the first reflected radar signal and a second reflected radar signal to create a plurality of bins based on frequencies or phases of the reflected radar signals, the bins corresponding to respective locations in the environment; identify a peak in a bin of the plurality of bins, the peak indicative of a presence of the subject; perform a comparison of the location and the bin with the peak; and steer the radar signals based on the comparison.

Example 30 includes the computer readable medium of any of Examples 26-29, wherein the instructions, when executed, cause the one or more processors to analyze phase information in the reflected radar signal to identify movements by the subject.

Example 31 includes the computer readable medium of any of Examples 26-30, wherein the vital sign is a first vital sign, and the instructions, when executed, cause the one or more processors to: determine the first vital sign based on a first range of movement; and determine a second vital sign based on a second range of movement, the second range of movement different than the first range of movement.

Example 32 includes the computer readable medium of any of Examples 26-31, wherein the second range of movement is larger than the first range of movement, the first vital sign is a heart rate and the second vital sign is a respiratory rate.

Example 33 includes the computer readable medium of any of Examples 26-32, wherein the radar antenna includes an array of antennas and the instructions, when executed, cause the one or more processors to steer the radar signals by energizing different subsets of the antennas used to transmit the radar signals.

Example 34 includes the computer readable medium of any of Examples 26-33, wherein the location is a first location and the radar antenna includes an array of antennas, and to steer the radar antenna, the instructions, when executed, cause the one or more processors to: energize a first subset of the antennas when the subject is in the first location; and energize a second subset of the antennas when the subject is in a second location in the environment.

Example 35 includes the computer readable medium of any of Examples 26-34, wherein the subject is a first subject, the vital sign is a first vital sign, and the radar antenna includes an array of antennas, and to steer the radar antenna, the instructions, when executed, cause the one or more processors to: energize a first subset of the antennas to measure the first vital sign of the first subject; and energize a second subset of the antennas to measure a second vital sign of a second subject.

Example 36 includes the computer readable medium of any of Examples 26-35, wherein the instructions, when executed, cause the one or more processors to measure the first vital sign and the second vital while the first subject and the second subject are in the environment at the same time.

Example 37 includes a method for non-contact sensing of vital signs, the method comprising: identifying a subject in an image; identifying a location of the subject in an environment of the image; non-mechanically steering a radar antenna toward the location; and determining a vital sign of the subject based on a reflected radar signal.

Example 38 includes the method of Example 37, including augmenting the image with data indicative of the vital sign to create an augmented image.

Example 39 includes the method Examples 37 or 38, including electronically outputting the augmented image to a display device.

Example 40 includes the method of any of Examples 37-39, wherein the reflected radar signal is a first reflected radar signal, and the method includes: processing the first reflected radar signal and a second reflected radar signal to create a plurality of bins based on at least one of frequencies or phases of the reflected radar signals, the bins corresponding to respective locations in the environment; identifying a peak in a bin of the plurality of bins, the peak indicative of a presence of the subject; performing a comparison of the location and the bin with the peak; and steering the radar signals based on the comparison.

Example 41 includes the method of any of Examples 37-40, including analyzing phase information in the reflected radar signal to identify movements by the subject.

Example 42 includes the method of any of Examples 37-41, wherein the vital sign is a first vital sign, and the method includes: determining the first vital sign based on a first range of movement; and determining a second vital sign based on a second range of movement, the second range of movement different than the first range of movement.

Example 43 includes the method of any of Examples 37-42, wherein the second range of movement is larger than the first range of movement, the first vital sign is a heart rate and the second vital sign is a respiratory rate.

Example 44 includes the method of any of Examples 37-43, wherein the radar antenna includes an array of antennas and the steering of the radar signals includes energizing different subsets of the antennas used to transmit the radar signals.

Example 45 includes the method of any of Examples 37-44, wherein the location is a first location and the radar antenna includes an array of antennas, and the steering the radar antenna includes: energizing a first subset of the antennas when the subject is in the first location; and energizing a second subset of the antennas when the subject is in a second location in the environment.

Example 46 includes the method of any of Examples 37-45, wherein the subject is a first subject, the vital sign is a first vital sign, and the radar antenna includes an array of antennas, and the steering the radar antenna includes: energizing a first subset of the antennas to measure the first vital sign of the first subject; and energizing a second subset of the antennas to measure a second vital sign of a second subject.

Example 47 includes the method of any of Examples 37-46, including measuring the first vital sign and the second vital while the first subject and the second subject are in the environment at the same time.

The following claims are hereby incorporated into this Detailed Description by this reference. Although certain example systems, methods, apparatus, and articles of manufacture have been disclosed herein, the scope of coverage of this patent is not limited thereto. On the contrary, this patent covers all systems, methods, apparatus, and articles of manufacture fairly falling within the scope of the claims of this patent.

What is claimed is:

1. An electronic device to measure vital signs, the electronic device comprising:
   a camera to capture an image;
   a radar antenna including an array of antennas; and
   at least one processor circuitry to:
      identify a subject in the image;
      identify a location of the subject in an environment;
      energize a first subset of the antennas when the subject is in a first location in the environment to steer radar signals toward the first location; and
      energize a second subset of the antennas when the subject is in a second location in the environment to steer radar signals toward the second location; and
      determine a vital sign of the subject based on a reflected radar signal.

2. The electronic device of claim 1, wherein one or more of the at least one processor circuitry is to augment the image with data indicative of the vital sign to create an augmented image.

3. The electronic device of claim 2, further including a display screen to present the augmented image.

4. The electronic device of claim 1, wherein the reflected radar signal is a first reflected radar signal, and one or more of the at least one the processor circuitry is to:
   process the first reflected radar signal and a second reflected radar signal to create a plurality of bins based on frequencies or phases of the reflected radar signals, the bins corresponding to respective locations in the environment;
   identify a peak in a bin of the plurality of bins, the peak indicative of a presence of the subject;
   perform a comparison of the location and the bin with the peak; and
   steer the radar signals based on the comparison.

5. The electronic device of claim 1, wherein one or more of the at least one processor circuitry is to analyze phase information in the reflected radar signal to identify movements by the subject.

6. The electronic device of claim 5, wherein the vital sign is a first vital sign, and one or more of the at least one processor circuitry is to:
   determine the first vital sign based on a first range of movement; and
   determine a second vital sign based on a second range of movement, the second range of movement different than the first range of movement.

7. The electronic device of claim 6, wherein the second range of movement is larger than the first range of movement, the first vital sign is a heart rate and the second vital sign is a respiratory rate.

8. The electronic device of claim 1, wherein the electronic device is physically distant from the subject.

9. The electronic device of claim 1, wherein the subject is a first subject, the vital sign is a first vital sign, and to steer the radar antenna, one or more of the at least one processor circuitry is to:
   energize one of the first subset of the antennas, the second subset of the antennas, or a third subset of the antennas to measure the first vital sign of the first subject; and
   energize another of the first subset of the antennas, the second subset of the antennas, or the third subset of the antennas to measure a second vital sign of a second subject.

10. The electronic device of claim 9, wherein one or more of the at least one processor circuitry is to measure the first vital sign and the second vital while the first subject and the second subject are in the environment at the same time.

11. The electronic device of claim 1, wherein the camera is to capture a plurality of images, and one or more of the at least one processor circuitry is to:
    determine if the subject is moving or still based on at least a subset of the plurality of images;
    determine the vital sign with a first accuracy if the subject is moving between the first location and the second location in the environment, and determine the vital sign with a second accuracy if the subject is still, the second accuracy greater than the first accuracy; and
    generate a report associating a probability with the vital sign based on the first accuracy or the second accuracy.

12. A non-transitory computer readable medium comprising instructions to cause one or more processors to at least:
    locate a first subject in an image;
    identify a location of the first subject in the image;
    control a radar antenna to steer the radar signals toward the location;
    energize a first subset of antennas to measure a first vital sign of the first subject based on a first reflected radar signal; and
    energize a second subset of the antennas to measure a second vital sign of a second subject based on a second reflected radar signal.

13. The computer readable medium of claim 12, wherein the instructions, when executed, cause one or more of the one or more processors to augment the image with data indicative of the first vital sign to create an augmented image.

14. The computer readable medium of claim 13, wherein the instructions, when executed, cause one or more of the one or more processors to output the augmented image to a display device.

15. The computer readable medium of claim 12, wherein the instructions, when executed, cause one or more of the one or more processors to:
    process the first reflected radar signal and a third reflected radar signal to create a plurality of bins based on frequencies or phases of the first and third reflected radar signals, the bins corresponding to respective locations in the environment;
    identify a peak in a bin of the plurality of bins, the peak indicative of a presence of the first subject;
    perform a comparison of the location and the bin with the peak; and
    steer the radar signals based on the comparison.

16. The computer readable medium of claim 12, wherein the instructions, when executed, cause one or more of the one or more processors to analyze phase information in the first reflected radar signal to identify movements by the first subject.

17. The computer readable medium of claim 16, the instructions, when executed, cause one or more of the one or more processors to:
    determine the first vital sign based on a first range of movement; and
    determine a third vital sign of the first subject based on a second range of movement, the second range of movement different than the first range of movement.

18. The computer readable medium of claim 17, wherein the second range of movement is larger than the first range of movement, the first vital sign is a heart rate and the third vital sign is a respiratory rate.

19. The computer readable medium of claim 12, wherein the location is a first location and to steer the radar antenna, the instructions, when executed, cause the one or more processors to:
    energize one of the first subset of the antennas, the second subset of the antennas, or a third subset of the antennas when the first subject is in a first location; and
    energize another one of the first subset of the antennas, the second subset of the antennas, or the third subset of the antennas when the first subject is in a second location.

20. The computer readable medium of claim 12, wherein the image is of an environment and the instructions, when executed, cause one or more of the one or more processors to measure the first vital sign and the second vital while the first subject and the second subject are in the environment at the same time.

21. A method for non-contact sensing of vital signs, the method comprising:
    identifying one or more subjects in an image;
    identifying a first location of a first one of the one or more subjects in an environment of the image;
    identifying a second location of a second one of the one or more subjects in the environment of the image;
    non-mechanically steering an array of radar antennas toward one or more of the first location or the second location by at least one of:
        (1) energizing a first subset of the antennas to measure a first vital sign of the first subject, and energizing a second subset of the antennas to measure a second vital sign of the second subject; or
        (2) energizing the first subset of the antennas when the first subject is in the first location, and energizing the second subset of the antennas when the first subject is in a second location in the environment; and
    determining one or more of the first vital sign or the second vital sign based on a reflected radar signal.

* * * * *

UNITED STATES PATENT AND TRADEMARK OFFICE
CERTIFICATE OF CORRECTION

Page 1 of 1

PATENT NO. : 12,343,127 B2
APPLICATION NO. : 17/724195
DATED : July 1, 2025
INVENTOR(S) : Andiappan et al.

It is certified that error appears in the above-identified patent and that said Letters Patent is hereby corrected as shown below:

In the Claims

In Column 27, Claim 4, Line 31, Delete "one the processor" and insert --one processor--.

Signed and Sealed this
Twenty-sixth Day of August, 2025

Coke Morgan Stewart
*Acting Director of the United States Patent and Trademark Office*